(12) United States Patent
Ransohoff et al.

(10) Patent No.: US 12,012,629 B2
(45) Date of Patent: Jun. 18, 2024

(54) CONTINUOUS PROCESSING METHODS FOR BIOLOGICAL PRODUCTS

(71) Applicant: Sartorius Stedim Chromatography Systems Ltd., Royston (GB)

(72) Inventors: Thomas C. Ransohoff, Lexington, MA (US); Marc A. T. Bisschops, Breda (NL)

(73) Assignee: Sartorius Stedim Chromatography Systems Ltd. (GB)

( * ) Notice: Subject to any disclaimer, the term of this patent is extended or adjusted under 35 U.S.C. 154(b) by 858 days.

(21) Appl. No.: 17/030,731

(22) Filed: Sep. 24, 2020

(65) Prior Publication Data

US 2021/0017561 A1 Jan. 21, 2021

Related U.S. Application Data

(63) Continuation of application No. 13/991,604, filed as application No. PCT/US2011/063598 on Dec. 6, 2011, now abandoned.

(Continued)

(51) Int. Cl.
| | |
|---|---|
| *C12M 3/00* | (2006.01) |
| *B01D 15/18* | (2006.01) |
| *B01D 15/38* | (2006.01) |
| *B01L 1/00* | (2006.01) |
| *C07K 1/36* | (2006.01) |
| *C07K 16/00* | (2006.01) |

(Continued)

(52) U.S. Cl.
CPC .......... *C12P 21/00* (2013.01); *B01D 15/1821* (2013.01); *B01D 15/3804* (2013.01); *C07K 1/36* (2013.01); *C07K 16/00* (2013.01); *C12M 23/44* (2013.01); *C12M 47/10* (2013.01); *C12M 47/12* (2013.01); *G01N 30/02* (2013.01)

(58) Field of Classification Search
CPC ...... G01N 30/468; G01N 30/02; C12M 47/10
See application file for complete search history.

(56) References Cited

U.S. PATENT DOCUMENTS

| | | | | |
|---|---|---|---|---|
| 4,722,902 A | * | 2/1988 | Harm | ..................... C12M 23/42 435/297.4 |
| 4,802,981 A | | 2/1989 | Kenney et al. | |

(Continued)

FOREIGN PATENT DOCUMENTS

| | | |
|---|---|---|
| JP | H09-509658 | 9/1997 |
| JP | H11-29494 | 2/1999 |

(Continued)

OTHER PUBLICATIONS

Bisschops et al., "Single-Use, Continuous-Countercurrent, Multicolumn Chromatography," *BioProcess International*, 7(Supp. 5):18-23 (Jun. 2009).

(Continued)

*Primary Examiner* — Nathan A Bowers
(74) *Attorney, Agent, or Firm* — Klarquist Sparkman, LLP

(57) ABSTRACT

The present invention is directed to the development of continuous processing technology for the purification of biopharmaceuticals and biological products, such as monoclonal antibodies, protein therapeutics, and vaccines. Methods for continuous processing of a biological product in a feed stream toward formulation of a purified bulk product are described.

8 Claims, 9 Drawing Sheets

Related U.S. Application Data

(60) Provisional application No. 61/420,066, filed on Dec. 6, 2010.

(51) Int. Cl.
   *C12M 1/00* (2006.01)
   *C12P 21/00* (2006.01)
   *G01N 30/02* (2006.01)

(56) References Cited

U.S. PATENT DOCUMENTS

| | | | |
|---|---|---|---|
| 5,256,294 A | 10/1993 | van Reis | |
| 5,429,746 A | 7/1995 | Shadle et al. | |
| 5,886,154 A | 3/1999 | Lebing et al. | |
| 5,928,516 A | 7/1999 | Hopkins et al. | |
| 6,012,487 A * | 1/2000 | Hauck | F16K 11/0853 137/625.46 |
| 6,139,746 A | 10/2000 | Kopf | |
| 6,432,630 B1 | 8/2002 | Blankenstein | |
| 8,549,934 B2 * | 10/2013 | Biksacky | G01N 1/2035 73/863.01 |
| 2003/0168107 A1 * | 9/2003 | Krog | G01N 21/05 137/599.03 |
| 2003/0229213 A1 | 12/2003 | Farrenburg et al. | |
| 2004/0241878 A1 | 12/2004 | Thommes et al. | |
| 2006/0273013 A1 * | 12/2006 | Chin | B01D 53/047 210/659 |
| 2007/0072285 A1 * | 3/2007 | Barringer | G01N 27/44704 435/286.5 |
| 2010/0135987 A1 | 6/2010 | Hickman et al. | |
| 2010/0206812 A1 * | 8/2010 | Woods | C10G 21/00 210/656 |
| 2010/0307334 A1 * | 12/2010 | Yang | G01N 30/461 96/104 |
| 2011/0198286 A1 | 8/2011 | Niazi et al. | |

FOREIGN PATENT DOCUMENTS

| | | |
|---|---|---|
| JP | 2006-507249 | 3/2006 |
| WO | WO86/00339 | 1/1986 |
| WO | WO2006/116886 | 11/2006 |
| WO | WO2007/089873 | 8/2007 |
| WO | WO2008/127087 | 10/2008 |
| WO | WO2008/128071 | 10/2008 |
| WO | WO2010/085893 | 8/2010 |
| WO | WO2011/046936 | 4/2011 |

OTHER PUBLICATIONS

Caillet-Fauquet et al., "Continuous-flow UVC irradiation: a new, effective, protein activity-preserving system for inactivating bacteria and viruses, including erythrovirus B19," *Journal of Virological Methods*, 118(2):131-139 (Jun. 2004).

Chin et al, "Simulated Moving Bed Equipment Designs," *Separation & Purification Reviews*, 33(2):77-155 (2004) (published online Aug. 2007).

Coffman et al., "Development of a Protein A SMB step for a Mab with up to 10 g/L titers," presented at BioManufacturing and Development conference, Boston, MA (Nov. 1-3, 2010).

Extended European Search Report for European Application No. 11846745.5, dated Jul. 7, 2016.

Fahrner et al., "Industrial Purification of Pharmaceutical Antibodies: Development, Operation, and Validation of Chromatography Processes," *Biotechnology and Genetic Engineering Reviews*, 18(1):301-327 (Feb. 2001).

Liu et al., "Recovery and purification process development for monoclonal antibody production," *MAbs*, 2(5):480-499 (Sep.-Oct. 2010).

Office Action for European Patent No. 11846745.5, dated Jul. 19, 2019.

Rathore et al., "Scale-Up and Optimization inBiopharmaceutical Applications," CRC Press, An Overview of Scale-Up, pp. 1-10 (Sep. 2002).

Trout et al., "Continuous Manufacturing of Small Molecule Pharmaceuticals: The Ultra-Lean Way of Manufacturing,", presented at MIT Leaders for Global Operations Conference, (Cambridge, MA) (Dec. 3-4, 2009).

Van Walsem et al., "Simulated moving bed in the production of lysine," *J. Biotech*, 59(1-2):127-132 (Dec. 1997).

Wallis et al., "Concentration of Viruses from Water by Membrane Chromatography," *Ann. Rev. Microbiol.*, 33:413-37 (Jan. 1979).

* cited by examiner

CONTINUOUS PROCESSING METHODS FOR BIOLOGICAL PRODUCTS

CROSS-REFERENCE TO RELATED APPLICATION

This is a continuation of U.S. patent application Ser. No. 13/991,604, filed Jun. 4, 2013, which is the U.S. National Stage of International Application No. PCT/US2011/063598, filed Dec. 6, 2011, which was published in English under PCT Article 21(2), which in turn claims the benefit of U.S. Provisional Application No. 61/420,066, filed Dec. 6, 2010, which are incorporated herein in their entireties.

FIELD OF THE INVENTION

The present invention is directed to the development of continuous processing technology for the production of biopharmaceutical and biological products, such as monoclonal antibodies and vaccines.

BACKGROUND OF THE INVENTION

Continuous processes are widely used in several industries, for instance the petrochemical, fine chemical, and agricultural processing industries. Distillation, plug flow reactions, chromatography, and adsorptive separations are all operated in continuous modes in large-scale industrial applications. For example, a well known large-scale simulated moving bed (SMB) purification process is the so-called Parex process, which separates para-xylene from a mixture of xylenes. This process is based on the Sorbex SMB technology developed and commercialized by UOP LLC (Des Plaines, IL (US)), Other notable examples of SMB or related continuous, counter-current chromatographic techniques are the purification of fructose from a mixture of glucose and fructose (which is used in the production of high fructose corn syrup); the recovery of sucrose and betaine from molasses; the purification of various carboxylic acids and amino acids; as well as the production of potassium nitrate for fertilizer.

One industry that has not benefitted significantly from continuous processing technology is the biopharmaceutical industry, where the final drug product is usually a large molecule (i.e., ≥3 kD) and must undergo several steps aimed at purification and, ultimately, sterilization, Until recently, the majority of biopharmaceutical and biological products have been manufactured and purified at very modest scale, obviating the need for moving away from inherently inefficient batch processing techniques. In recent years, however, the commercial success of the first monoclonal antibody therapeutics, coupled with the desire to implement fully disposable or single-use components in manufacturing processes, has driven increased interest in more efficient processing technologies.

Advances in simulated moving bed separation processes, such as the integrated BioSMB™ system (Tarpon Biosystems, Inc., Worcester, MA (US)), have made it possible to convert separation process steps that were traditionally operated in batch mode into SMB processes that can be run continuously, taking a clarified feed and purifying in a continuous fashion a target molecule such as a monoclonal antibody or a vaccine to yield a purified intermediate product ready for additional downstream processing toward a final, purified bulk drug product and finally a packaged, sterile pharmaceutical product. The BioSMB™ system provides a flexible, programmable system for replacing a batch purification process step. It provides the advantages of great reductions in scale of operations, great reductions in solvent use and the amount of chromatography media required, and the ability to employ fully disposable components (thereby reducing the investment in stainless steel components, as well as minimizing downtime otherwise taken up in cleaning and refurbishing permanent components).

The capabilities for continuous processing afforded by improved SMB systems has led to increased interest in converting other stages of the overall biopharmaceutical processing to continuous processing methods. Production of a biopharmaceutical typically begins with production of the proteinaceous product in a bioreactor, followed by many stages, or unit operations, each designed to separate the product from undesired components and impurities.

Interest in the use of single-use or "disposable" technologies has increased significantly in recent years due to the time and capital savings offered by these technologies along with other benefits. However, as the capacity of industrial scale disposable bioreactors has leapt forward, the equipment designs for disposable downstream processing (that is, processing of the culture grown in a bioreactor to end in a final packaged product) have lagged behind. For example, while new bioreactors capable of 2,000 liter cell cultures are now on the market and 5,000 liter capacity disposable bioreactors are being designed, the largest disposable downstream chromatography columns currently available are not large enough (ca. 30 cm diameter) to process the output from a modern "high titer" (e.g., 5 g/L of target protein) 2,000 liter disposable bioreactor run. A cell culture grown in a 2,000 liter bioreactor having a concentration of protein product at 5 g/liter or higher, may provide more than 10 kg of protein material for purification.

Continuous processing would permit significant reductions in the scale of equipment needed downstream from the bioreactor, and accordingly the need for novel methods of continuous processing for all phases of biopharmaceutical production is acute.

SUMMARY OF THE INVENTION

The present invention is related to the development of a novel continuous processing technology (CPT) for the purification of biopharmaceuticals and biological products for increasing manufacturing productivity and efficiency in the biopharmaceutical industry.

The novel CPT processes described herein have been developed for the purification of biopharmaceuticals and will advantageously allow for an entire purification process to be operated continuously using disposable processing elements.

A preferred element for the design of continuous processing systems is the utilization of multi-valve arrays, preferably in the form of an integrated valve cassette or manifold. Such valve cassettes are illustrated by the BioSMB™ system, which integrates dozens of diaphragm-style valves into a single disposable block, resulting in an "integrated circuit" approach to fluid control in continuous chromatography applications. See, e.g., FIGS. 10A-10E, By separating the disposable valve cassette and integrated diaphragm membrane sheet from the permanent actuator block, the BioSMB™ system design enables sophisticated fluid control with a fully-disposable flowpath that meets the stringent performance and cleanability requirements of the biopharmaceutical industry.

The block flow diagram shown in FIG. 2 illustrates the multiple processing steps or unit operations of a CPT process of the present invention. FIG. 2 illustrates the purification of a monoclonal antibody product, but it will be readily appreciated that the principles of continuous processing described herein can be applied to the purification of any biological product.

In one embodiment, the present invention is directed to a process for the production of a biological product comprising:
(a) continuously transferring a biological product-containing solution to a first unit operation capable of separating the solution into two or more fractions comprising at least one fraction containing said biological product and at least one fraction containing one or more components of the biological product-containing solution desired to be separated from said biological product, wherein said first unit operation has at least one inlet and at least one outlet and is configured to permit continuous fluid flow between said at least one inlet and at least one outlet;
(b) continuously transferring the flow from at least one outlet of said first unit operation to a second unit operation having at least one inlet for receiving flow from at least one outlet of said first unit operation, said flow from said first unit operation comprising said biological product, said second unit operation capable of separating the product received through said at least one inlet into two or more fractions comprising at least one fraction containing said biological product and at least one fraction containing one or more components of the product received through said at least one inlet desired to be removed from said biological product, and wherein said second unit operation further has at least one outlet and is configured to permit continuous flow between said at least one inlet and at least one outlet, and wherein the throughput of said second unit operation is equal to the output flow received from said first unit operation; and
(c) recovering a fluid fraction containing said biological product.

According to this embodiment, independently for each transferring step, the transferring step comprises directing the flow from the preceding unit operation to an intermediate storage vessel, wherein the vessel has a holding capacity equal to or less than half of the volume received from the preceding unit operation during processing of one entire lot.

In another embodiment, the present invention is directed to a method for the manufacture of a biological product in a continuous process system comprising the steps of:
(a) producing conditioned media containing a biological product in a bioreactor;
(b) continuously removing cells and cell debris from the conditioned media to produce a clarified solution comprising the biological product;
(c) continuously transferring the clarified solution to a first unit operation, the operation comprising a capture chromatography process comprising
    (1) contacting said product solution with an affinity ligand capable of complexing with said biological product and
    (2) dissociating complexes of the affinity ligand and said biological product formed in said contacting step to produce a purified biological product solution;
(d) continuously transferring the purified biological product solution to a second unit operation comprising a low pH incubation process comprising
    (1) collecting at least part of the purified biological product solution in an incubation receptacle,
    (2) adjusting the pH of the purified biological product solution to a pH calculated to inactivate any viruses contained in the solution, and
    (3) readjusting the pH of the purified biological product solution to produce a virus-inactivated biological product solution;
(e) continuously transferring the virus-inactivated biological product solution to a series of additional downstream processing steps, which at least comprises one anion exchange chromatography process;
(f) continuously transferring the product of the downstream process to a sixth unit operation comprising a nanofiltration process; and
(g) continuously transferring the product of the nanofiltration process to a seventh unit operation comprising microfiltration through a 0.2 μm filter to produce a stable purified biological product.

In one embodiment the removal of cells and cell debris in step (b) is carried out by a centrifugation process.

In another embodiment of the method, the first unit operation is a simulated moving bed affinity chromatography process.

In another embodiment, the present invention is directed to a method for incubating a solution for a controlled period of time, the method comprising:
(a) continuously transferring the biological product solution into a first incubation receptacle;
(b) adjusting the solution conditions to achieve the desired incubation conditions in the first receptacle;
(c) continuously transferring the content of the first receptacle into a second receptacle or alternatively, into a series of receptacles, or a length of tubing, with a collective volume for a desired residence time;
(d) continuously transferring the content of the second receptacle into a third receptacle; and
(e) adjusting the solution conditions to the desired conditions for the subsequent or next unit operation.

In yet another embodiment, the present invention is directed to a method for incubating a biological product solution at desired solution conditions for a controlled period of time and within a desired tolerance time window, the method comprising:
(a) continuously transferring the biological product solution into a series of incubation receptacles wherein the volume of each receptacle is equal to or less than the flow rate times the desired tolerance time;
(b) discontinuing flow to the inlet of said receptacle and adjusting the solution conditions to the desired incubation solution condition in said receptacle while mixing to ensure solution homogeneity;
(c) holding each receptacle for the desired incubation time;
(d) readjusting the solution conditions in each receptacle to the desired conditions for processing in the subsequent unit operation, while mixing to ensure solution homogeneity; and
(e) transferring the incubated biological product solution from each receptacle to the subsequent unit operation In yet another embodiment, the present invention is directed to an apparatus for connecting two or more unit operations of a manufacturing process for continuous processing, the apparatus comprising:
(a) a valve manifold providing at least three fluid transmission channels comprising a central channel traversing said valve manifold and having an inlet end and an outlet end, a priming channel connecting a separate inlet with said central channel, and a bypass channel connecting a separate outlet with said central channel, each of the channels having at least one independently actuatable valve for independently opening or closing the channel, the central channel inlet being suitable for receiving throughput from an upstream unit operation, and the priming channel inlet being suitable for receiving fluid for filling the priming channel and the central channel; and (b) at least one surge receptacle having at least one inlet and at least one outlet, said surge receptacle inlet being connected to the central channel outlet of said valve manifold, and said at least one surge receptacle having the capacity to hold the throughput of a unit operation connected to said valve manifold central channel inlet, In one embodiment, the surge receptacle further comprises a vent outlet communicating the inside of said receptacle with the ambient environment. In one embodiment, a filter may be interposed between said vent outlet and the ambient environment, and wherein the vent outlet further comprises a valve for opening and closing the outlet. Further, the surge receptacle outlet may be connected to a pump.

In another embodiment, the bypass channel of the apparatus is connected to a bypass collection receptacle having the capacity to hold the throughput of a unit operation connected to said valve manifold central channel inlet.

In yet another embodiment, the present invention is directed to an apparatus for connecting two or more unit operations of a manufacturing process for continuous processing, the apparatus comprising:

(a) a valve manifold providing at least five fluid transmission channels comprising a central channel traversing the valve manifold and having an inlet end and an outlet end, a priming channel connecting a separate inlet with the central channel, a surge receptacle inlet channel connecting a separate inlet with the central channel, a surge receptacle outlet channel connecting a separate outlet with the central channel, and a bypass channel connecting a separate outlet with the central channel, and wherein each of the five channels has at least one independently actuatable valve for independently opening or closing the channel, the central channel inlet being suitable for receiving throughput from an upstream unit operation, said priming channel inlet being suitable for receiving fluid for filling said priming channel and said central channel;

(b) at least one surge receptacle having at least one inlet and at least one outlet, wherein a surge receptacle inlet is connected to the surge receptacle outlet channel of the valve manifold, and a surge receptacle outlet is connected to the surge receptacle inlet channel of the valve manifold, and wherein the at least one surge receptacle has the capacity to hold the throughput of a unit operation connected to the valve manifold central channel inlet. The at least one surge receptacle may further comprise a vent outlet communicating the inside of said receptacle with the ambient environment. In one embodiment, a filter is interposed between the vent outlet and the ambient environment, and wherein the vent outlet further comprises a valve for opening and closing said outlet. In another embodiment, the connection between the surge receptacle outlet and the surge receptacle inlet channel of the valve manifold is equipped with a pump for regulating fluid flow along the connection.

In yet another embodiment, the bypass channel outlet of the apparatus is connected to a bypass collection receptacle having the capacity to hold the throughput of a unit operation connected to the valve manifold central channel inlet.

In another embodiment, the present invention is directed to a continuous processing system comprising:

(a) a first apparatus for carrying out a first unit operation, the apparatus comprising:
(1) a plurality of valve modules, each module having a central channel traversing the module and a plurality of branch channels connecting the central channel with the outside of the valve module, wherein each of the channels has at least one independently actuatable valve for independently opening or closing the channel, and wherein the valve of the central channel separates the inlet end of the central channel from the outlet end of the central channel, and wherein at least two branch channels connect separate inlets to the valve module with the central channel on the inlet side of the central channel valve and at least two branch channels lead from the central channel on the outlet side of the central channel valve to separate outlets from the valve module;
(2) a plurality of solution conduits, each conduit connecting to a separate branch channel of each valve module, and
(3) a plurality of chromatography columns, each column having an inlet and an outlet, wherein the column inlet is connected to the inlet end of a valve module central channel and the column outlet is connected to the outlet end of the central channel of a different valve module, such that the plurality of columns is connected in series through intervening valve modules and wherein the outlet of the last column in the series is connected, via an intervening valve module, to the inlet of the first column in the series;

(b) a second apparatus for carrying out a second unit operation comprising:
(1) one or more incubation receptacles each having at least one inlet and at least one outlet, wherein collectively the one or more incubation receptacles has at least the capacity to hold the output of said first unit operation:
(2) a valve module comprising an inlet and an outlet, an inlet channel connected to the valve module inlet, and one or more inlet branch channels connecting with the inlet channel, wherein each inlet branch channel leads from the inlet channel and connects to an inlet of one of the one or more incubation receptacles, and wherein each of the inlet branch channels has at least one independently actuatable valve for independently opening or closing the channel, the valve module further comprising an outlet channel leading to the valve module outlet, and one or more outlet branch channels connecting with the outlet channel, wherein each outlet branch channel leads from the outlet channel and connects to an outlet of one of the one or more incubation receptacles, wherein each of the outlet branch channels has at least one independently actuatable valve for independently opening or closing the channel; and (c) a third apparatus, for connecting the output of said first apparatus to the inlet of said second apparatus, the third apparatus comprising:
(1) a valve module providing at least five fluid transmission channels comprising a central channel traversing the valve module and having an inlet end and an outlet end, a priming channel connecting a separate inlet with the central channel, a surge receptacle inlet channel connecting a separate inlet with the central channel, a surge receptacle outlet channel connecting a separate outlet with the central channel, and a bypass channel connecting a separate outlet with the central channel, and each of the five channels having at least one independently actuatable valve for independently opening or closing the channel, wherein the central channel inlet is connected to an outlet branch channel of each of the plurality of valve modules of the apparatus of said first unit operation, the priming channel inlet being suitable for receiving fluid for filling the priming channel and the central channel, (2) at least one surge receptacle having at least one inlet and at least one outlet, wherein a surge receptacle inlet is connected to the surge receptacle outlet channel of the valve module, and a surge receptacle outlet is connected to the surge receptacle inlet channel of the valve module, and wherein the at least one surge receptacle has the capacity to hold the output of the apparatus of the first unit operation, and wherein the central channel outlet of the valve module is connected to the inlet of the valve module of the apparatus for carrying out the second unit operation.

In one embodiment of the continuous processing system, the at least one surge receptacle and/or the one or more incubation receptacles further comprises a vent outlet communicating the inside of the receptacle with the ambient environment. In one embodiment, a filter is interposed between the vent outlet and the ambient environment, and wherein the vent outlet further comprises a valve for opening and closing the outlet. In yet another embodiment, the connection between the surge receptacle outlet and the surge receptacle inlet channel of the valve manifold is equipped with a pump for regulating fluid flow along said connection.

In another embodiment of the continuous processing system of the present invention, the bypass channel outlet is connected to a bypass collection receptacle having the capacity to hold the throughput of a unit operation connected to the valve manifold central channel inlet.

In yet another embodiment of the continuous processing system described herein, the plurality of valve modules of the apparatus for carrying out the first unit operation are integrated into a master valve manifold.

In yet another embodiment of the continuous processing system described herein, the one or more incubation receptacles is equipped with means for mixing the contents of the receptacle. For example, the means for mixing the contents of the receptacle may be a rocker table.

In another embodiment of the continuous processing system described herein, any of said receptacles may be a single-use receptacle.

The novel CPT processes described herein have been developed for the purification of biopharmaceuticals and will advantageously allow for an entire purification process to be operated continuously using disposable processing elements.

A preferred element for the design of continuous processing systems is the utilization of multi-valve arrays, preferably in the form of an integrated valve cassette or manifold. Such valve cassettes are illustrated by the BioSMB™ system, which integrates dozens of diaphragm-style valves into a single disposable block, resulting in an "integrated circuit" approach to fluid control in continuous chromatography applications. See, e.g., FIGS. 10A-10E. By separating the disposable valve cassette and integrated diaphragm membrane sheet from the permanent actuator block, the BioSMB™ system design enables sophisticated fluid control with a fully-disposable flowpath that meets the stringent performance and cleanability requirements of the biopharmaceutical industry.

The block flow diagram shown in FIG. 2 illustrates the multiple processing steps or unit operations of a CPT process of the present invention. FIG. 2 illustrates the purification of a monoclonal antibody product, but it will be readily appreciated that the principles of continuous processing described herein can be applied to the purification of any biological product.

BRIEF DESCRIPTION OF THE DRAWINGS

In FIG. 11, flow to receptacle 52 is shown, and independent flow from receptacle 50 to outlet 54 is shown. The dotted lines signify lines (flowpaths) that are not in use.

DETAILED DESCRIPTION OF THE INVENTION

Figure 1:
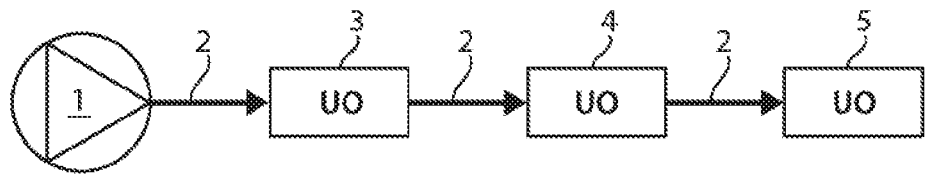
FIG. 1 is a schematic diagram illustrating the concept of continuous processing according to the invention as an interlinked cascade of processing steps or unit operations (UO).

The present invention provides processes that can be adapted to the manufacture of a biological product which make at least two or more steps of the processing of the biological product continuous. Continuous processing allows the manufacturer to conduct the manufacturing process using less material and relying on equipment of a reduced scaled compared to the equipment that would be required for batch operations. Continuous processing reduces downtime in the overall manufacturing process and thus reduces cycle times from the beginning of a manufacturing run to production of bulk drug substance or packaging of the final product.

In order that the invention may be more clearly understood, the following abbreviations and terms are used as defined below.

The term "biological product" as used herein refers to a product of interest created via biological processes or via the chemical or catalytic modification of an existing biological product. Biological processes include cell culture, fermentation, metabolization, respiration, and the like. Biological products are typically comprised of proteins. Biological products of interest include, for example, antibodies, antibody fragments, proteins, hormones, vaccines, fragments of natural proteins (such as fragments of bacterial toxins used as vaccines, e.g., tetanus toxoid), fusion proteins or peptide conjugates (e.g., such as subunit vaccines), virus-like particles (VLPs) and the like.

The term "biopharmaceutical" as used herein refers to a biological product purified and formulated so as to be physiologically acceptable for use as a drug or therapeutic agent.

The term "unit operation" as used herein refers to a manufacturing process step designed to separate an undesired element from a product of interest or designed to ensure that a composition containing a product of interest is substantially free of an undesired component. Such unit operations in the manufacture of a biopharmaceutical after creation, e.g., in a bioreactor, may include, without limitation: primary recovery operations, such as centrifugation, microfiltration, depth filtration, etc., for clarification of the output from a cell culture bioreactor; capture chromatography, for example by affinity chromatography, size exclusion chromatography, ion exchange chromatography, hydrophobic interaction chromatography (HIC), immobilized metal affinity chromatography (IMAC), and the like; incubation at low pH (e.g., pH 3.0-3.5) or other solution conditions for achieving, e.g., inactivation of viruses, protein refolding, aggregate dissociation, and the like; micro- or nano-filtration, etc., for filtration of viruses, bacteria, particulates and other contaminants or impurities; tangential flow filtration for product concentration (e.g., by ultrafiltration); buffer exchange (e.g., by diafiltration); "polishing" or intermediate chromatography or membrane adsorption operations (e.g., by ion exchange), for clearance of variant products (e.g., heavy chain dimers in solution with a tetrameric antibody product); clearance of aggregates; clearance of DNA or host cell proteins; virus adsorption; removal of product-specific impurities; filtration for bulk storage (e.g., 0.2 micron filtration); and similar operations. A single unit operation may be designed to accomplish multiple objectives in the same operation.

The term "upstream" or "upstream process" refers to the step(s) of biopharmaceutical manufacture relating to the creation of the active biological product by a biological process or other reaction. Ordinarily, the biological product to be isolated and processed into a biopharmaceutical is the result of a fermentation or is the expression product of a recombinantly transformed host cell. Thus, the upstream portion of the manufacturing process typically relates to the production of a target protein (such as an antibody, an active protein or protein fragment, a fusion protein, virus-like particle, etc.) either in a prokaryotic or eukaryotic cell that naturally produces the (endogenous) target protein or, more commonly, in a prokaryotic or eukaryotic host cell which has been transformed by recombinant DNA technology to express an exogenous target protein or proteins, Upstream processes involving creation of a biological product in cell culture will be conducted in a fermentor or bioreactor, and the upstream process may be a batch process (e.g., batch or fed-batch cell culture grown in a fermentor) or a continuous process (e.g, perfusion cell culture)

The term "downstream" or "downstream processing" refers to the steps following "upstream" processing of a biological product that are required to separate the biological product from impurities and contaminants, typically resulting in production of a bulk drug substance. Downstream processing refers to some or all the steps necessary for capture of a biological product from the original solution in which it was created, for purification of the biological product away from undesired components and impurities, for filtration or deactivation of pathogens (e.g., viruses, endotoxins), and for formulation and packaging.

The term "continuous process" as used herein refers to any process having two or more processing steps in series, wherein the output from an upstream step (unit operation) is transferred to a downstream step (unit operation) and wherein it is not necessary for the upstream processing step to run to completion before the next processing step is started. In a continuous process some portion of the target product is always moving through the processing system. Ideally, the flow through a continuous process is regulated so that, to the greatest extent possible, every step or unit operation of the continuous process is running at the same time and at substantially the same production rate. In this way, compression of the cycle time is maximized and the shortest possible completion time is achieved. Accordingly, the expressions "continuous transfer" or "transferred continuously", referring to a product stream moving from an upstream unit operation to a downstream unit operation, means that the connections or links between the two unit operations are such that the upstream unit operation transfers a product stream (directly or through other components) to the second (downstream) unit operation, and that the downstream unit operation begins before the upstream unit operation runs to completion (that is, the two successive unit operations are processing the product streams flowing into them simultaneously for at least part of the overall process run of which the two unit operations comprise a part).

The Continuous Processing Technology ("CPT") described herein represents a fundamental improvement over existing batch biopharmaceutical manufacturing processes and will deliver substantial benefits in capital and time savings and in process flexibility and scalability. The adoption of CPT enables biopharmaceutical production facilities to handle biological product production runs at ton-scale levels with far less capital investment than in conventional batch manufacturing processes. CPT also enables the manufacture of biopharmaceuticals for clinical testing to be achieved more quickly and cost-effectively.

Reducing the capital investment required to establish biornanufacturing capacity improves return on capital and reduces operating costs, which should eventually lead to lower biopharmaceutical prices. By improving the efficiency of early-stage clinical trial manufacturing, more new biopharmaceuticals will be able to enter clinical trials, improving development pipelines for larger companies and reducing the time and cost to achieving proof-of-concept for smaller companies. Speeding the development of new medicines and reducing their cost of production has a significant impact on both the quality and affordability of biopharmaceuticals.

The CPT processes described herein provide the means to handle the ton-scale output which is now possible by utilization of multiple disposable bioreactors. By adopting the continuous processing methods described herein, manufacturers of a biological product can avoid the typical $500 million/5-year investment required to build a new facility capable of ton-scale biopharmaceutical production by conventional batch methods using large scale, stainless steel equipment. Reduction in capital investment of up to 80% and compression of the time to scaled-up production capacity to approximately 2 years can be achieved based on the reduced scale of equipment required to operate continuous processes. A company that is developing a new biological product faces the challenge of funding the scale-up and manufacture of the product from laboratory scale quantities to the much larger quantities necessary for preclinical experiments and clinical trials. Since the risk of failure at this point in development is high (i.e., fewer than 20% of biopharmaceuticals that enter clinical trials receive approval for commercial sale), companies developing new drug candidates (and their investors) are reluctant to spend any more capital than is absolutely necessary to advance product candidates into clinical trials. Additionally, since manufacturing and development activities are almost always on the critical path prior to initiation of human clinical testing for new biopharmaceuticals, the ability to streamline and increase the speed of producing clinical supplies has significant value in the pre-IND stage of development.

The requirements for GMP manufacturing of clinical supplies for use in human clinical testing translate to a significant cost for most early-stage programs, and delay or failure in achieving GMP standards can contribute to difficulty in financing or gaining approval to proceed with planned clinical studies. The use of continuous processing, coupled with the use of disposable technologies such as described herein, has helped reduce capital outlays and has increased the speed for achieving clinical manufacturing.

Construction of a disposables-based clinical manufacturing facility may cost as little as $15-20 million, as compared to a cost of $30-50 million for conventional clinical manufacturing facilities. The CPT processes described herein can further reduce these costs and also speed up the clinical manufacturing process by shrinking the scale of equipment required to produce the needed quantities of product, and by making the entire manufacturing process more flexible and more portable.

Because these improvements disclosed herein lead to lower investment requirements and shorter times for clinical supply manufacturing, the return profile for development of early-stage biopharmaceuticals will be improved for both large companies with in-house manufacturing capacity as well as for smaller companies who may outsource the manufacture of their products. This improved return profile will enable more promising biological product candidates to enter clinical testing: larger companies will be able to move more product candidates into early-stage testing, expanding the number of drug candidates entering drug development pipelines; and small or start-up biopharmaceutical companies seeking to demonstrate proof-of-concept based on human clinical studies as a prerequisite to financing or partnering objectives will be more able to pass this hurdle.

Enabling Implementation of Disposables

The introduction of disposables (or single-use technologies) into biopharmaceutical manufacturing processes constitutes an important shift away from standard reusable technologies. The use of disposables technology is driven by industry-wide needs to reduce capital investment, to increase speed of development, and to reduce contamination due to re-use of production equipment. Adoption of disposable technologies in small-scale, clinical manufacturing applications has been relatively rapid, owing to both the relative ease of implementation as well as to the significant benefits of capital and time savings. As described above, the lack of availability of sufficiently large disposable purification equipment presents a "bottleneck" to implementation of larger-scale processes using disposable technology.

The CPT processes described herein enable more complete use of disposables. Continuous processing permits reduction in the scale of equipment necessary to process the currently large and increasing capacity of bioreactors (2,000 liters presently, moving to 5,000 liters and above). Continuous processing allows downstream processing to proceed utilizing available equipment, including single-use (disposable) equipment; also, the flow-through capacity of CPT allows for productivities matching and significantly exceeding that of the largest bioreactors, enabling greater penetration of fully-disposable processes. The switch from traditional batch processing to continuous processing fundamentally changes the way the biopharmaceutical industry develops and manufactures its products.

Configurations for continuous processing are disclosed herein which are specifically adapted to the use of disposable components. In many instances disposable components will have lower tolerances or reduced capacity in comparison to permanent, reusable equipment, and several features for continuous processing have been designed so that the disposable components can be used and any differences in their properties accommodated by the system. As one example, single-use plastic tubing may be used to replace stainless steel tubing, however the tolerance to systemic pressure drops from unit operation to unit operation is much lower for plastic tubing than for stainless steel tubing. In the present invention, features such as surge receptacles useful to vent the system and return a given connection to atmospheric pressure are incorporated so that no tubing failures or loss of system performance results from the substitution of plastic tubing for stainless steel tubing.

Continuous Unit Operations

Unit operations in the manufacturing process of a biological product can benefit from continuous multicolumn or multistage operation. This has been demonstrated for the capture chromatography step by conversion from a batch operation to continuous counter-current simulated moving bed (SMB) chromatography. In a batch operation, the several steps of a capture chromatography operation, such as Protein A capture of an IgG target using Protein A affinity chromatography, are performed serially: Clarified conditioned media from a bioreactor is applied to a capture chromatography column, followed by wash, elution, cleaning (regeneration), and equilibration steps, with each step being completed before the next step is begun. In a SMB multicolumn system, multiple columns are employed and the multiple steps are run simultaneously on different columns, Utilizing a continuous flow, multicolumn system permits the capacity of the columns to be reduced, thus allowing a large bioreactor volume to be processed using small diameter columns (instead of scaling up column size to accommodate the feed of a bioreactor by batch capture chromatography). The operation of such a SMB multicolumn system is illustrated in FIGS. 10A-10E.

A commercial SMB system (BioSMB™ system, Tarpon Biosystems, Inc., Worcester, MA (US)) has been developed which provides an integrated array of valves and connections (valve cassette) for coordinating flow of multiple solutions and buffers to a multiplicity of interconnected columns, enabling scalable, continuous chromatography operation using a wide range of separation media. The BioSMB™ system is programmable and adjustable, and it is useful for converting virtually any single-column batch operation to a continuous multicolumn operation. The BioSMB™ system also makes full use of disposable components by featuring replaceable tubing, columns, and valve membrane, all of which can be quickly disconnected from the system for installation of new components, thereby reducing or virtually eliminating system downtime.

At the heart of the BioSMB™ system is a valve cassette that acts as an integrated circuit for fluid handling, incorporating the many valves required to enable continuous processing into a single disposable-format valve array. (Such a valve array is illustrated schematically in FIGS. 10A-10E, where each of the square items 108 represents a valve. An array of 54 valves (108) housed in a single valve cassette or manifold is thus depicted, although it will be appreciated the larger valve cassettes (or smaller, repetitive valve modules) can be employed. The commercial BioSMB™ system valve manifold, for instance, features 240 separately actuatable valves.) This valve cassette has proven to be a robust and cleanable device, suitable for meeting the stringent requirements of biopharmaceutical applications.

FIG. 1 depicts schematically the broadest aspect of continuous processing according to the present invention. In continuous processing, a cascade of process steps or unit operations (UO) are directly connected to each other in series. An outlet of the first unit operation (3) is directly connected via line (2) to the inlet of the next unit operation (4), and the flowthrough from a second unit operation (4) proceeds from an outlet of that unit operation (4) to an inlet of a third unit operation (5). This illustration shows three processing stages or unit operations (3, 4, 5), interconnected by a line (tubing or flowpath) (2), with product flow driven by a single pump (1). For a biopharmaceutical product, the process culminates (e.g., after unit operation 5) in a pharmaceutically acceptable formulation of a biological product, in a form ready for administration to a patient. As depicted in the schematic diagram, each unit operation is connected in series to the next unit operation; the first unit operation (3) receives the output from a previous step, which may be a batch step, or the throughput of the pump (1); the throughput of the first unit operation (3) is directed to the inlet of the next unit operation (4), and the throughput that unit operation (4) is direct to the inlet of a third unit operation (5). It is understood that each UO of the diagram may represent several processing steps, and it will also be appreciated that additional unit operations may be added to the series of unit operations until a complete process is assembled. In the continuous processing methods of the invention, the throughput of one unit operation is connected to the input of the next unit operation so that the connected unit operations may run continuously, so that the desired product of interest moves from one unit operation to the next without the necessity of waiting for the one unit operation to be completed before introduction of product to the next unit operation for further processing is started.

The size of the bioreactor sets the initial volume of medium that will have to be processed in a biological product manufacturing process. In a batch process, the mass of the product is the most significant factor, however in a continuous process the volume of medium to be processed determines the scale of all the downstream operations. Therefore the greater the titer of product, the greater are the advantages gained by adopting a continuous process. Currently, 5 grams of product per liter (5 g/L) is considered a high titer for protein products such as monoclonal antibodies, although optimizing host cell production, media conditions, growth cycles, etc. has yielded titers of 10-13 g/L or higher.

It is pointed out that continuous processing systems according to the invention do not require constant flow from one unit operation to the next or constant flow through all of the interconnected unit operations. For any number of reasons, the rate of flow through a unit operation or between unit operations may need to be adjusted or halted. Continuous processing only requires that the links between two unit operations are such that the first or upstream unit operation transfers a product stream (directly or through other components) to the second (downstream) unit operation, and that the downstream unit operation begins before the upstream unit operation runs to completion (that is, for at least part of the manufacturing run, the two successive unit operations are processing product simultaneously). Although continuous processing does not require uniform or uninterupted flow through all of a series of connect unit operations, it is preferable if the processing system can be operated so as to maintain as continuous a flow through the system as possible. Features are described herein that allow a high degree of uninterrupted How between unit operations of an overall continuous process to be achieved.

Figure 2A:
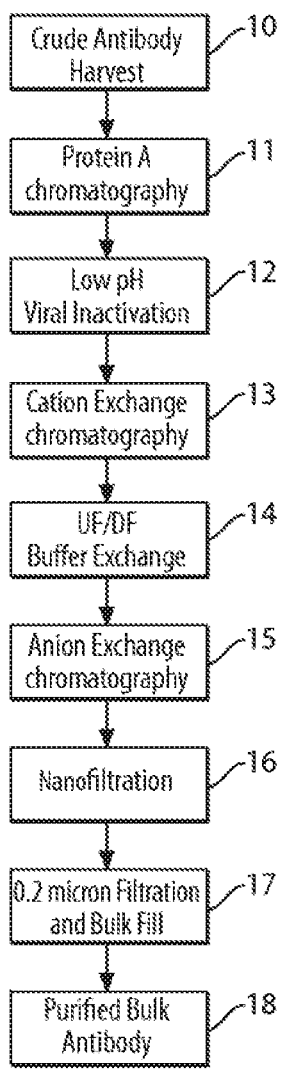
FIG. 2A is a block flow diagram illustrating an example of an interlinked series of unit operations with the object of producing a purified monoclonal antibody product. Continuous processing of an antibody from the production of a crude antibody-containing solution (conditioned medium) in a bioreactor (10) through several processing steps culminating in bulk storage of purified antibody product (18) is depicted.

FIG. 2A is a block flow diagram of an exemplary manufacturing process for a biopharmaceutical. In the process illustrated, by way of example, the biopharmaceutical is a monoclonal antibody. Each block of the diagram represents a unit operation, and the sequence of operations (10-18) shown represents a cascade of connected unit operations that are running continuously and to the greatest extent possible simultaneously, so that ideally no shutdown or interruption of the process occurs, and no unit operation needs to be delayed to wait for a previous operation to be completed (as in batch processes). The sequence of specific unit operations depicted in FIG. 2A is typical and suitable for monoclonal antibody processing. It will be appreciated that different biological products will be manufactured according to a process comprising different unit operations, or similar unit operations performed in a different order. For example, if the target biological product is produced in bacterial culture and is initially created as an aggregate or inclusion body within the host cells, the primary recovery may involve such unit operations as pelleting of the cells via centrifugation or ultrafiltration, lysing the cells, harvesting the inclusion bodies, dissociation of aggregates (e.g., with a chaotropic agent), and protein refolding, all occurring before a capture chromatography operation. Moreover, a capture chromatography unit operation will be tailored to the particular protein product and may involve a suitable affinity ligand other than Protein A (which selectively binds the constant fragment (Fc) of immunoglobulins) or may involve a different chromatography altogether (e.g., IMAC, HIC, ion exchange, and the like). Likewise, the downstream processing of different products may suitably involve different steps and a different series of unit operations. The design of suitable processing stages for production of a desired biological product is within the capabilities of practitioners in this field; linking the processing stages (unit operations) so as to be capable of continuous processing of the biological product is the subject of the present invention.

Referring again to the monoclonal antibody process illustrated in FIG. 2A, the first block (10) represents a bioreactor in which a cell culture is produced, for example, by growing transformed host cells (e.g., yeast cells, Chinese Hamster Ovary cells, etc.) that express and preferably secrete the antibody into the cell culture medium. The conditioned medium containing the secreted biological product is usually clarified, e.g., by centifugation and/or microfiltration or depth filtration, to remove cells and cell debris before being transferred to the next unit operation (11). The next block (11) represents a capture chromatography step, which for immunoglobulins is advantageously performed using Protein A affinity chromatography. The throughput of the Protein A chromatography step (11) is fed continuously to the next unit operation (12), which in this illustration is a viral inactivation step. Because antibodies captured on Protein A media are commonly eluted using a low pH eluant (e.g., 100 mM glycine at pH 3,0-pH 3.5), low-pH viral inactivation is a logical unit operation to follow continuously from Protein A capture and elution. The throughput from viral inactivation (12) is transferred continuously (after adjustment of the solution to suitable conditions (i.e., pH) for loading onto the next chromatography step) to the next unit operation (13), which in this illustration is cation exchange chromatography, designed to eliminate product-related impurities such as aggregates and degraded or improperly assembled antibodies. Cation exchange is a logical unit operation at this stage for an antibody production process, but for other biological products another type of chromatography operation may be more effective. For example, hydrophobic interaction chromatography (HIC), ceramic hydroxyapatite (CHT), or other types of chromatography steps may be substituted at this stage for particular purposes. The throughput from the cation exchange chromatography step (13) is transferred continuously to the next unit operation (14), which in this illustration is an ultrafiltration/diafiltration step. Ultrafiltration is designed to concentrate the antibody product by retention of the product on a tangential flow membrane, followed by diafiltration used for buffer exchange. Desired new buffer is added at the same rate as removal of water/buffer through the permeate, so the volume and concentration stay constant while buffer is being exchanged. The throughput from the ultrafiltration/diafiltration step (14) is transferred continuously to the next unit operation (15), which in this illustration is anion exchange chromatography, designed to eliminate impurities having a net negative charge, such as DNA, endotoxin, viruses, and host cell proteins. Antibodies usually have a relatively high isoelectric point, therefore conditions may be readily adjusted so that the antibody product has a net positive charge while the impurities exhibit a net negative charge (and thus antibody flows through the positively charged medium/membrane of an anion exchange column or membrane). The throughput from the anion exchange chromatography step (15) is transferred continuously to the next unit operation (16), which in this illustration is a nanofiltration step, e.g., using a 20 nm-40 nm sterile membrane filter, designed for removal of viruses. The throughput from the nanofiltration step (16) is transferred to the next unit operation (17), which in this illustration is an optional concentration/buffer exchange followed by microfiltration (0.2 μm filter), designed to put the purified monoclonal antibody into a solution for bulk storage (18). The bulk purified antibody in a storage-stable formulation (18) is ready for transfer to a sterile fill operation that will perform further operations, such as additional formulation as necessary, sterilizing filtration, and filling the antibody into sterile vials, syringes or other containers for distribution as a biopharmaceutical product, In a manufacturing process such as illustrated in FIG. 2A, chromatography steps will advantageously be operated using a programmable multicolumn regulatory system, such as the aforementioned BioSMB™ system (Tarpon Biosystems, Inc., Worcester, MA (US)), which will enable continuous operation. A preferred system for the ultrafiltration/diafiltration steps is Cadence™ system (Pall Corp., Port Washington, NY (US)). An integrated valve cassette such as featured in the BioSMB™ system can also be adapted to regulate continuous operation of the final nanofiltration and microfiltration steps.

Figure 2B:
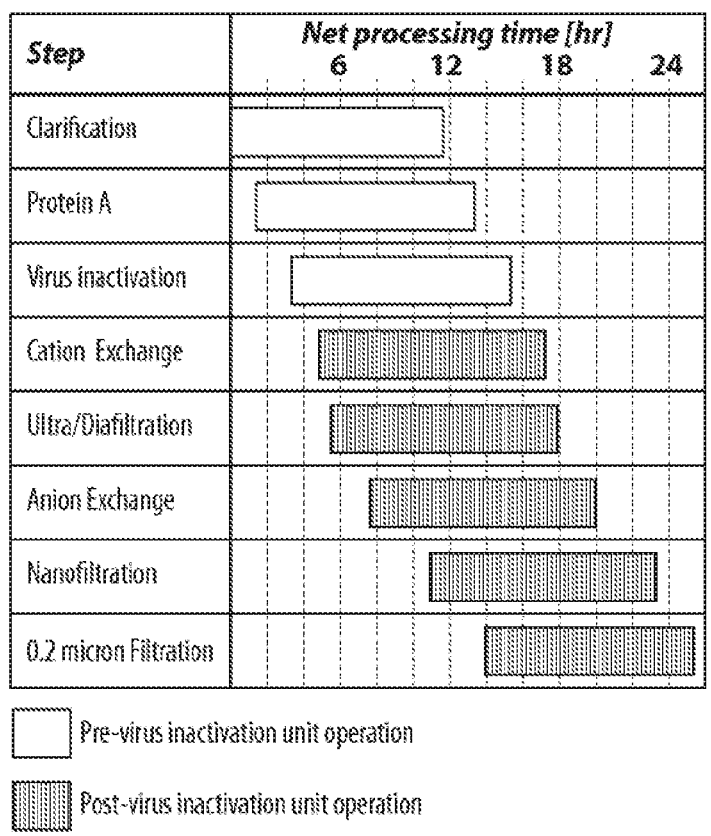
FIG. 2B illustrates the compression of net processing time achieved by continuous operation of the unit operations illustrated in FIG. 2A. Whereas batch processing requires that each successive unit operation cannot begin until the processing of the preceeding unit operation is completed, the continuous processing methods permit the target biological product to be continuously moved through each of the successive processing steps as it begins to emerge from the previous operation. As a result, several if not all unit operations are active at the same time, and the overall production process that would require at least several days to complete via batch methods can be operated with continuous processing so that final purified bulk drug product is being produced within a matter of hours. Additionally, due to the continuous nature of the operation, the scale of equipment required is significantly reduced compared to what is required for batch operations.

Referring to FIG. 2B, timecourse plots for each of the unit operations diagrammed in FIG. 2A are shown, and the feature that successive unit operations begin before the previous unit operation ends illustrates the advantages gained by continuous processing. Whereas in a manufacturing process conducted using batch operations, each of the timecourses would need to run to completion before a collected product could be transferred to the next batch step, and none of the timecourses would overlap. Batch manufacturing on the scale illustrated would take up to four days or more to complete. By contrast, the continuous processing methods allow overlapping timecourses, with substantial periods of connected unit operations running simultaneously. When continuous processing is maximized, the four day batch manufacturing process is completed in about 24 hours.

Figure 3:
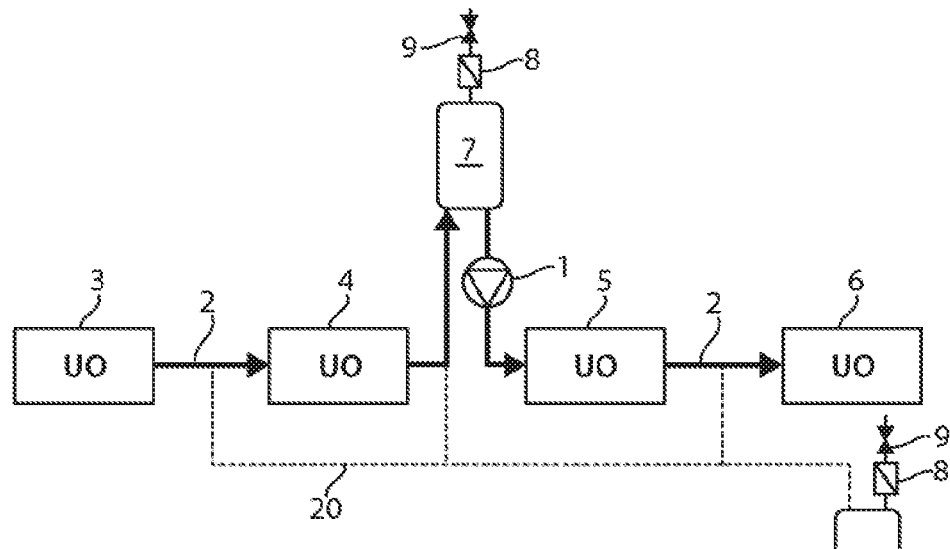
FIG. 3 is a schematic diagram of a continuous processing system showing two additional features, namely, a surge receptacle (7) for regulating flow between unit operations and relieving back pressure, and an emergency collection receptacle (21) for providing a means for rescue of partially processed biological product in case of a system failure or upset.

Referring to FIG. 3, a series of four unit operations (UO) is illustrated schematically. The system illustrated is equipped with two additional features aiding continuous operation. One feature is a surge receptacle (7) connected between two unit operations, so that the output of the second unit operation (4) is collected in receptacle (7). The receptacle (7) is equipped with a sterilizing grade filter (8), e.g., a 0.2 micron filter, that is permeable to air but screens out microorganisms. When the valve (9) is opened to the air, the pressure inside the receptacle (7) is equalized to ambient (atmospheric) pressure. The contents of the receptacle, at atmospheric pressure, can be fed via pump (1) to the next unit operation (5) at a lower pressure drop than would be necessary to overcome back pressure from flow maintained through downstream unit operations (5) and (6) in a closed system running without the surge receptacle (7).

In continuous processes utilizing single-use equipment, suitable surge receptacles (7) and transmission lines (tubing, 2) will commonly be made out of less durable materials, such as plastic. In such instances, the receptacle (7) may be a plastic bag (surge bag) or a vented plastic bottle. Such plastic materials and their connections between unit operations will have less resistance to back pressure build-up than, for instance, stainless steel containers and tubing; therefore, the use of surge receptacles to alleviate systemic pressure and lower the pressure drop necessary to maintain flow from one operation to the next is highly advantageous not only for regulating continuity of flow but for preserving the integrity of the system and avoiding material or connection failures.

Referring again to FIG. 3, the second feature aiding continuous flow through the entire system is the installation of a bypass collection receptacle (21), together with the transmission conduits (20) making it possible to divert the flow from any unit operation (UO) so that the partially processed product is not lost if transfer of the flow to the next intended unit operation is not possible, for example, due to a clog, a downstream contamination, a connection failure, determination of the need for continued incubation, of similar upset in the normal operation of the continuous process. Installation of a bypass collection receptacle (21) provides a means of rescuing a product that has undergone partial processing in one or more unit operations but that would be lost if the product flow were passed through a downstream stage that had become unsuitable for receiving the product due to contamination, blocked flow, leakage, unprepared downstream unit operations, etc. The partially processed product captured in the bypass receptacle (21) can be introduced into the cascade of unit operations at the point it was diverted, thus avoiding the loss of yield and cost of reprocessing that would occur if the manufacturing process had to be stopped, reset and started over. Advantageously, a separate return line (not shown) and a pump if necessary may be provided for return of a product solution collected in the bypass receptacle (21) to any point in the cascade of unit operations.

Figure 4:
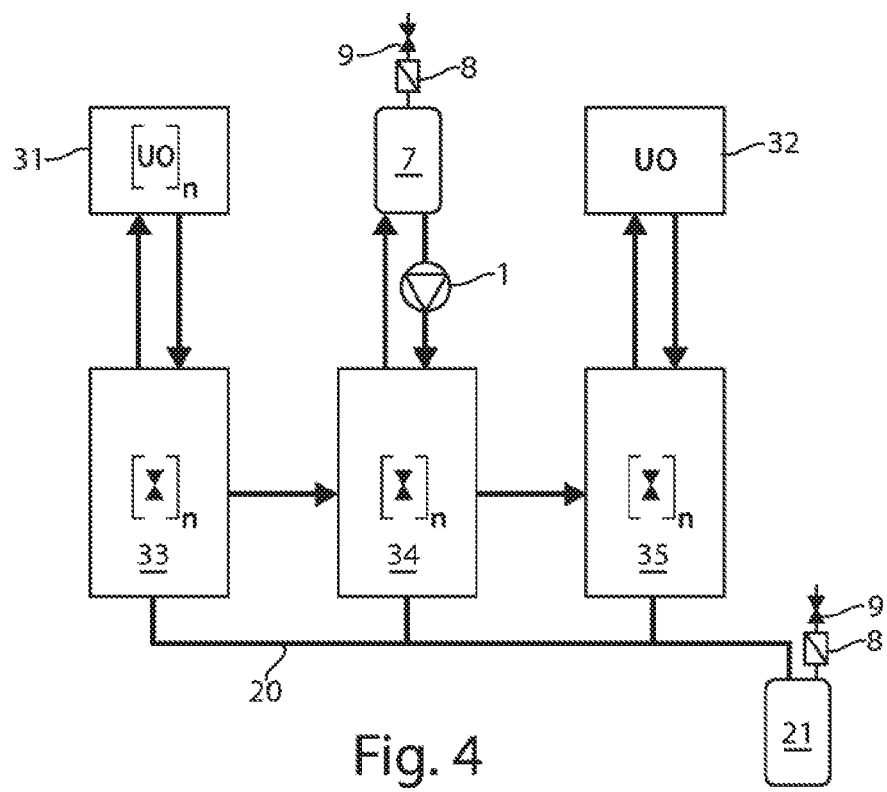
FIG. 4 is a schematic diagram of a continuous processing system according to the invention wherein the processing steps (UO) are integrated using multi-valve valve modules (33, 34, 35). In the system depicted, the surge receptacle (7) is connected to a separate valve module (30), making it an optional operation in the processing path.

FIG. 4 illustrates a manufacturing process featuring a surge receptacle (7) and a bypass collection container (21) as in FIG. 3, however in this figure the surge receptacle (7) is connected to the process through a valve module (34) providing sufficient valves and connections, represented by $[A]_n$, to direct the flow of upstream unit operations (31) either directly to the succeeding unit operation (32), via line (2), or alternatively to an intermediate surge receptacle (7). This system thus treats the surge receptacle (7) as an intermediate optional unit operation between the upstream unit operations (31) and the downstream unit operation (32). In the figure, $[UO]_n$, signifies a plurality of n unit operations located upstream, with their input and output regulated by repetitive valve modules (33). Preferably the repetitive valve modules illustrated (i.e., 33, 34, 35) will be identical modules, which will standardize the connections and flowpaths between unit operations, simplify process programming, and provide a component for regulating unit operation flow that is easily replaceable.

Figure 5:
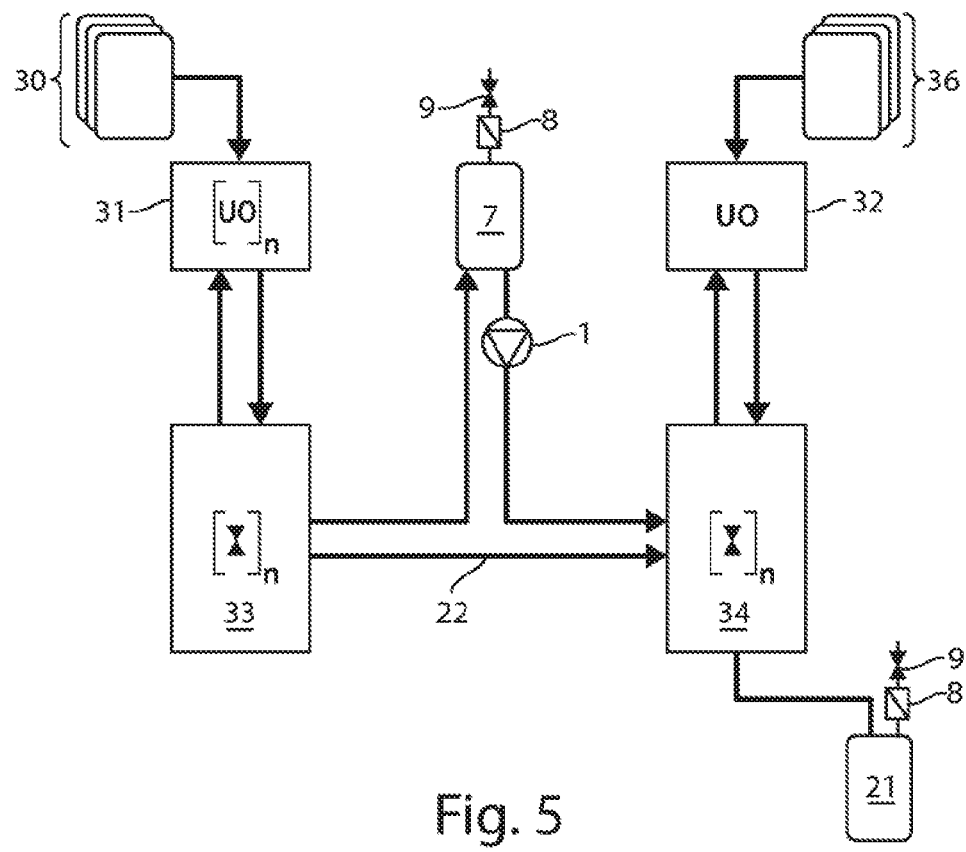
FIG. 5 is a schematic diagram of an alternative continuous processing system according to the invention wherein flow to a surge receptacle (7) is not separately regulated by a separately controlled valve system. Instead, the throughput from the preceding unit operation (31) is either directed to the surge receptacle (7) or directed to the final unit operation (32) (bypassing the surge receptacle) using the valve system (33) of the preceeding unit operation.

Referring to FIG. 5, an alternate embodiment of a continuous process according to the invention is illustrated schematically, in which a surge receptacle feature (7) is connected as a separate unit operation, however the use of the surge receptacle (7) is made optional by providing connections from upstream unit operations (31) regulated via the valve module (33) that lead to the surge receptacle (7) via input line (2) or alternatively lead directly to the downstream unit operation (32) via a separate line (20). Each unit operation (UO) is connected to a series of containers or reservoirs providing the input solutions (buffers, wash solutions, elution buffers, equilibration solutions, solvents, and the like) that are necessary and appropriate for running each step of a unit operation. The collections of input solutions are represented schematically by items 30 and 36; each set of input solutions will be different, since they will be tailored to the steps of a particular unit operation, although a solution that is common to a number of unit operations may of course be connected to more than one unit operation. The flow of the various input solutions may advantageously be regulated via an integrated valve manifold (not shown) which may preferably be the same valve manifold that regulates links from one unit operation to the next unit operation (e.g., 33, 34). In FIG. 5, an emergency bypass collection receptacle (21) is also provided, and the connections leading from each unit operation to the receptacle (21) are made via valve modules (33, 34).

Figure 6:
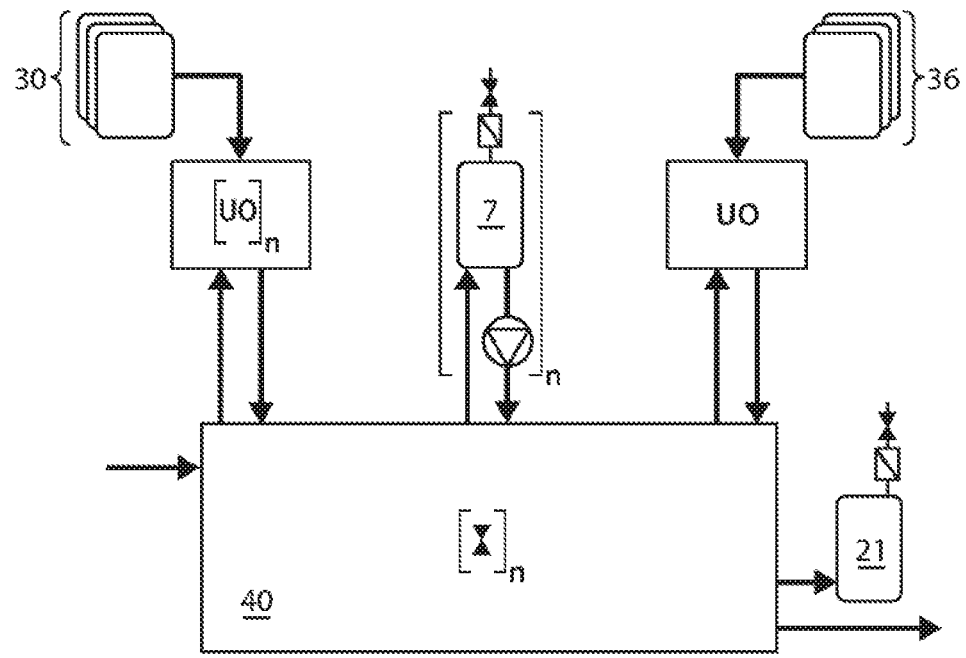
FIG. 6 is a schematic diagram of an alternative continuous processing system according to the invention, which differs from the systems depicted in FIGS. 4 and 5, in that a master valve manifold (40) regulates flow to and from a number (n) of unit operations (U0) (31), regulates flow direction to a number (n) of surge receptacles (7), regulates flow from preceeding unit operation(s) (31) or surge receptacle (7) to a downstream unit operation (32), and regulates emergency bypass to a collection receptacle (21), enabling the rescue of partially processed biological product.

Referring to FIG. 6, an alternate embodiment of a continuous process according to the invention is illustrated schematically, in which a plurality of surge receptacles (7) is connected to the system, and a master valve manifold (4) having a multiplicity of valves, $[A]_n$, interconnects the entire series of unit operations (UO), surge receptacles (7), and a bypass collection tank or receptacle (21).

Figure 7:
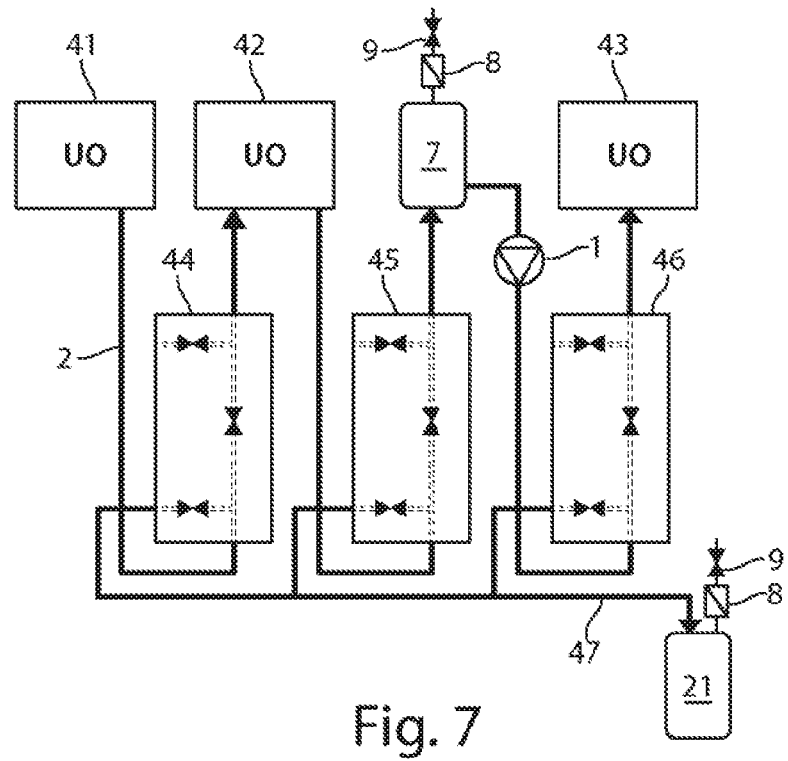
FIG. 7 is a schematic diagram of part of a continuous biological product manufacturing process showing four unit operations interconnected via multi-valve regulator modules (44, 45, 46), In this embodiment a surge receptacle (7) is disposed as a separate unit operation between two processing steps, i.e., unit operations (UO) 42 and 43. Alternate valving directs flow between any two unit operations to an emergency cutoff receptacle (21) by directing flow along the bypass line (47).

Referring to FIG. 7, a manufacturing process or part of a manufacturing process comprising three unit operations (41, 42, 43) is depicted schematically. The connections linking the unit operations and other features are regulated by separate valve modules (44, 45, 46). Preferably each valve module is identical, making connections uniform and simplifying replacement of any individual valve module. More preferably, the connections linking unit operations will be integrated into one master valve manifold (not shown), allowing all unit operations to be run according to a single integrated valve switching program. In FIG. 7, each of the valve modules (44, 45, 46) has channels and appropriate valves for directing flow to the desired features. The output of the first unit operation (41) is directed via an input line (2) leading through a central channel of its associated valve module (44) directly to the next unit operation (42). Closure of the central valve and opening the side valve to bypass line (47) provides a circuit to divert the output of the first unit operation (41) to bypass collection receptacle (21). The valve module (44) also has separate controllable flowpath for priming buffer to aid in maintaining constant flow to the next unit operation (42) if the feed from the previous unit operation (41) is not ready, interrupted or diverted. The second unit operation (42) is connected via its valve module (45) to a surge receptacle (7). The valve module (45), having a similar format to the other valve modules (44, 46), also provides bypass collection and priming buffer flowpaths. The surge receptacle (7), being vented through sterilizing grade filter (8) and pinch valve (9), returns the pressure of this segment of the system to atmospheric pressure. The output from surge receptacle (7) can thereafter be pumped with a low pressure drop to the next unit operation (43) via the pump (1). The output from the surge receptacle (7) may be directed through the valve module (46) directly to the unit operation (43) or diverted via line (47) to the bypass collection receptacle by appropriate manipulation of the valves. As in the other valve modules (44, 45), the final illustrated valve module (46) a separate flowpath for priming buffer is also provided.

Figure 8:
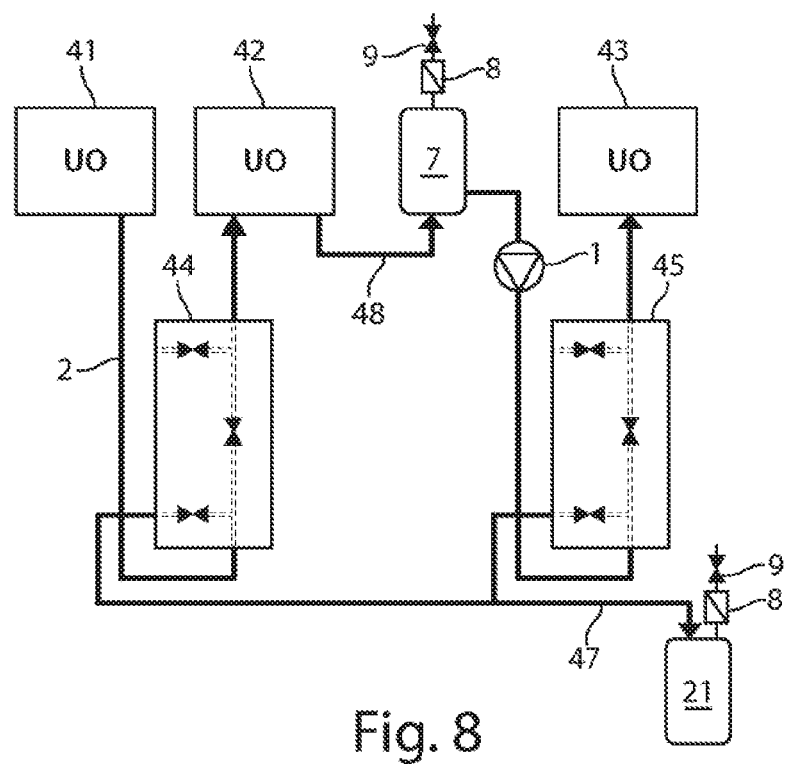
FIG. 8 is a schematic diagram of part of a continuous biological product manufacturing process showing three unit operations (UO) interconnected in an alternate plan to that of FIG. 7. In this embodiment, the intervening surge receptacle (7) between unit operation (42) and unit operation (43) is a permanent fixture through which the output of preceeding unit operation (42) must pass prior to transfer to the last unit operation (43) shown here. The surge receptacle (7) of this scheme is thus not an optional operation.

FIG. 8 shows an alternative embodiment for a series of three unit operations (UO) in a continuous manufacturing process according to the invention. In this embodiment a surge receptacle (7) as in FIG. 7 is connected to receive the flowthough from the second unit operation, via a direct input line (48). The surge receptacle (7) this is a non-optional step between the upstream unit operation (42) and the downstream unit operation (43).

Figure 9:
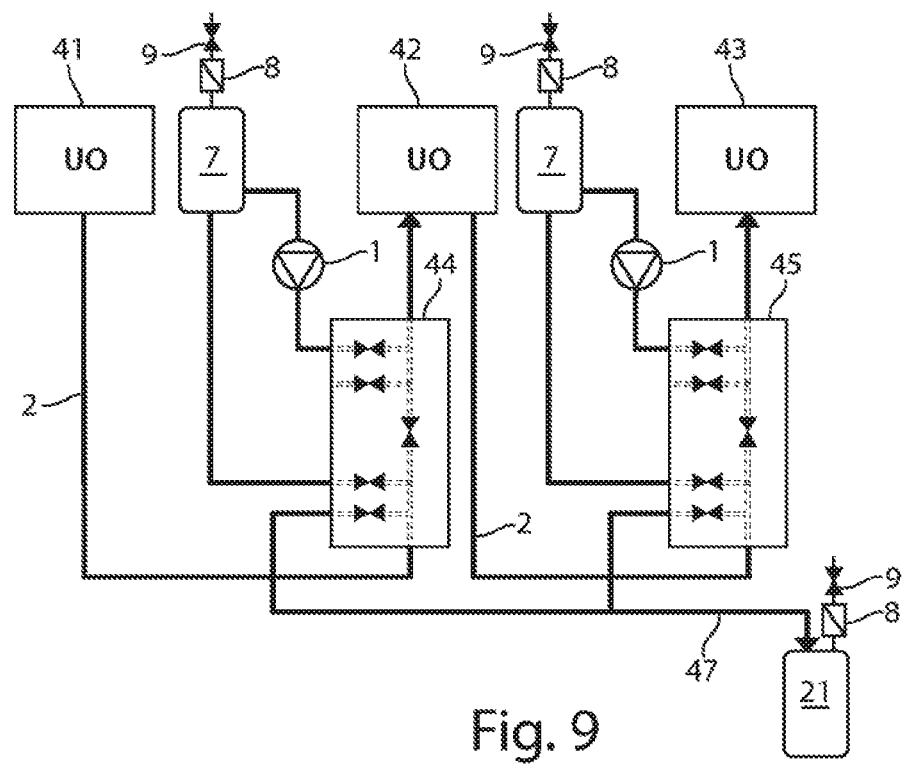
FIG. 9 is a schematic diagram of part of a continuous biological product manufacturing process showing three unit operations (UO) interconnected in an alternate plan to that of FIG. 7. In this embodiment, flow from one unit operation (UO) to the next is regulated by connection to identical multi-valve valve manifolds (44) having common inlets (48), e.g., for priming buffer, and common outlets (47) leading to a collection receptacle (21). Each valve manifold has inlets and outlets to effect bypass of the throughput received from the previous unit operation (e.g., 41) to a surge receptacle (7) prior to transfer via pump (1) to the succeeding unit operation (e.g., 42). Repetitive valve modules (44) may be supplanted by a unitary master valve manifold (not pictured) which would integrate all of the valving represented by valve modules (44) into a single manifold programmable to accommodate all of the desired transfer and bypass operations.

Referring to FIG. 9, a series of three unit operations (UO) in a manufacturing process is illustrated. The repetitive valve modules (44, 45) have additional channels and valves placing a surge receptacle (7) on a separate circuit, thus making diversion of flow to the surge receptacle (7) and thence to the downstream unit operations (42 or 43) optional. Such a circuit allows for delaying flow from an upstream unit operation to the next downstream unit operation or provides a means for equalizing back pressure building from a downstream unit operation.

The connection schemes illustrated in FIGS. 7, 8, and 9 show advantages of utilizing integrated, repetitive valve modules for linking unit operations. The product stream can be diverted to alternative paths for alternative processing, additional processing, or holding, or for emergency rescue of the partially processed product in case of a downstream system failure or upset. The surge receptacles serve to collect product-containing fluid and allow a pump to take said fluid out of the (non-pressurized) surge receptacle in a controlled manner. With this feature, the cumulative pressure drop across a series of unit operations (which would be the sum of the pressure drops of the individual unit operations) can be kept lower, so that disposable components (usually having a low pressure rating) can be used anywhere in the process. Another function of the surge receptacles is to create a stable flow into the next unit operation (through the pump) even if the previous unit operation does not produce a stable, steady product flow. With many unit operations, for instance capture chromatography, a product stream is not always continuously running out of the system. Instead, the outflow from a unit operation may instead come in repetitive intervals. On average there is a continuous flow, but the cyclic nature of, e.g., a multicolumn process allows for intermittent flow of product. These fluctuations in the outflowing product stream from a unit operation are dampened by intervening surge receptacles, which gives the operator a means for controlling and making more uniform the input into a downstream unit operation. It can be seen that providing an optional surge bag circuit as depicted in FIG. 9 connecting to each unit operation provides a mechanism for making a series of unit operations into a continuous process, even where one or more of the component operations does not provide a continuous, steady output to be transferred to downstream unit operations. The surge receptacle thus becomes a useful feature for designing continuous processes.

The surge receptables will have a volume that permits the operator to minimize the effect of any fluctuations in flow resulting from the previous unit operation. For instance, in case the previous unit operation is a multicolumn chromatography process, such as an SMB process, the capacity of the surge receptacle is preferably chosen such that it can accommodate multiple (e.g., three) consecutive peaks of the eluate of the SMB process. The surge receptacle preferably is equipped with means to release air from the surge receptacle without allowing contaminants to enter the surge receptable. One way to achieve this (illustrated in FIGS. 7, 8, 9) is to provide the surge receptacle with an outlet that is equipped with a sterilization grade microfilter (8), e.g., 0.2

μm pore size filter. The outlet of that filter is then preferably equipped with a valve (9), e.g., a pinch valve, for a controlled air release. Releasing air from the system is particularly important during start-up procedures to displace air from all the equipment and instruments.

Continuous Capture of Biological Product

One of the initial unit operations in any biological product manufacturing process will be a capture step, which typically follows the primary recovery step of a manufacturing process. As noted above, the capture unit operation is commonly an affinity chromatography process, but depending on the target biological product it can also advantageously utilize any other suitable separation technique, such as hydrophobic interaction chromatography (HIC), immobilized metal affinity chromatography (IMAC), ion exchange chromatography, and the like. Affinity capture and elution requires a series of steps, including column loading (i.e., with a feed stream containing the target), washing, and elution, and after elution cleaning (regeneration) of the chromatography media and equilibration is often desired, so that the system can undergo repeated cycles without replacement of columns.

Simulated moving bed chromatography provides a way of continuous processing in a capture unit operation. The continuous purification of a capture target is aided by adoption of integrated valve modules, such as the valve manifold featured in the BioSMB™ chromatography system (Tarpon Biosystems, Inc). The computer-assisted valve manifold can be programmed for automatic switching of column feeds between feed stream, wash buffer, elution buffer, cleaning buffer, and equilibration buffer, to create the simulated moving bed separation. Such a system is illustrated schematically in FIGS. 10A-10E, which shows a four zone SMB chromatography unit operation conducted using six columns loaded with capture media (see, 1, 2, 3, 4, 5, 6 in FIG. 10A). The six columns are interconnected in series through an integrated valve manifold, which is represented as an array of individually actuatable valves (108), accordingly the array depicted in FIGS. 10A-10E shows 54 valves (108).

Figure 10A:
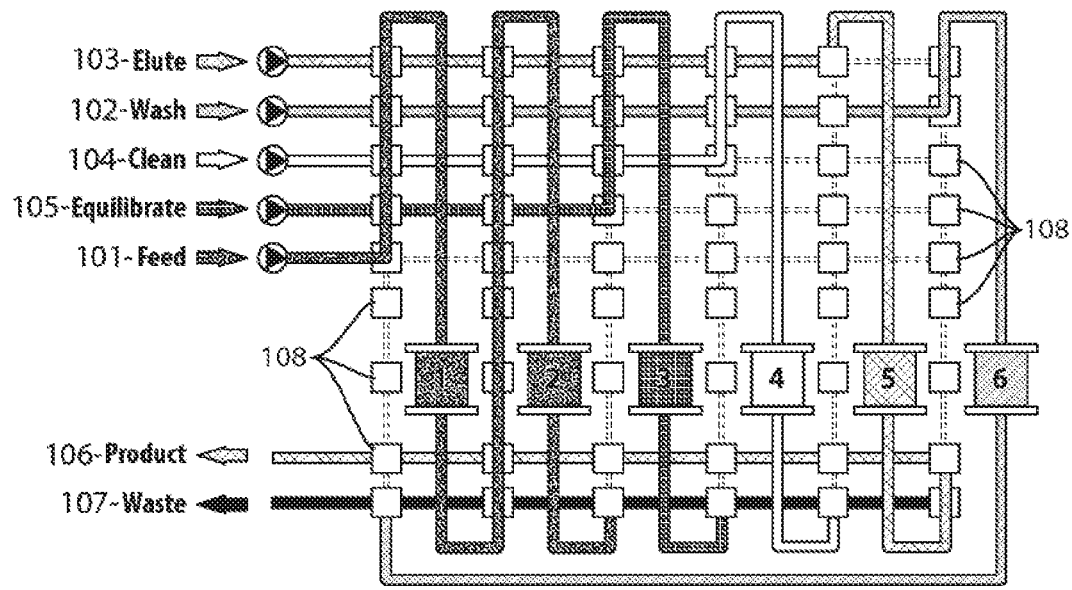
FIGS. 10A-10E is a schematic representation of the use of an integrated valve cassette to regulate operation of a continuous counter-current multi-column simulated moving bed chromatography process. 10A, 10B, 10C, 10D, and 10E represent sequential steps in a simulated moving bed chromatography process involving six columns.

Referring to FIG. 10A, the valve manifold has at least five inlets, e.g., so as to accomodate, in the system illustrated, inputs from a product feed stream (101), a wash solution (102), an eluant (103), a cleaning solution (104), and an equilibration buffer (105). Output lines for recovery of product and for drawing off waste solutions (106 and 107, respectively) are also shown.

Continuous operation of a column chromatography purification process is illustrated by consideration of FIGS. 10A-10E in succession. Referring to FIG. 10A, the feed stream (101) is directed through the valve manifold along a fluid pathway formed by appropriate actuation of valves (108) leading to the first affinity separation column (1). The first column (1) has its outlet connected, through the valve manifold, to the inlet of the second column (2), and both columns receive input from the feed stream until the bed of at least the first column (1) becomes saturated with affinity-captured biological product.

Figure 10B:
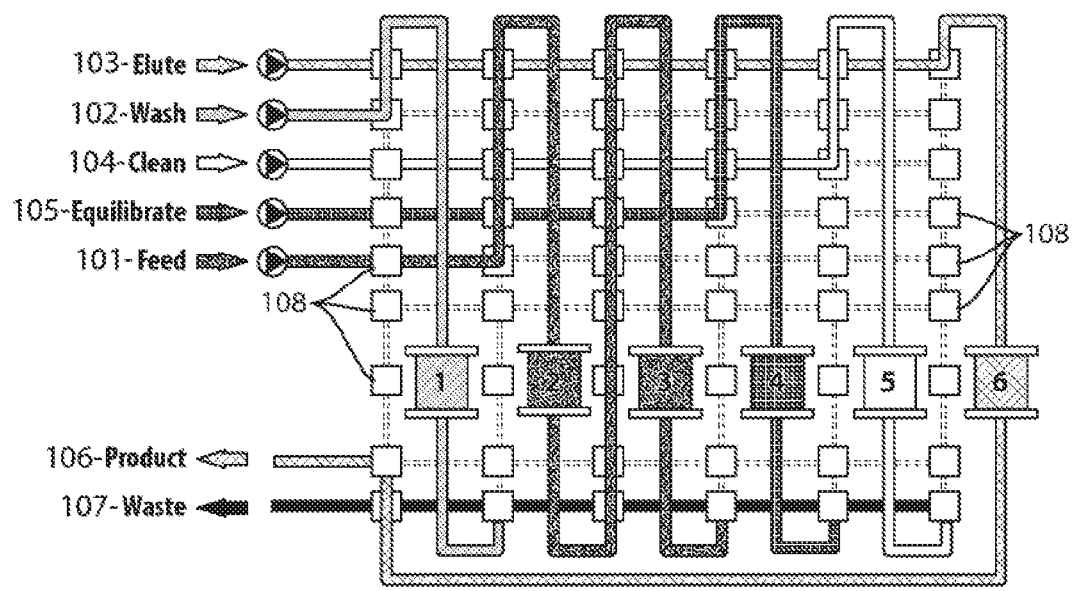

Referring to FIG. 10B, after saturation of the first column (1) bed, the valving of the valve manifold is switched to shift the input to the first column (1) from the feed stream (101) to a wash solution (102). Simultaneously, the second column (2) continues to receive the feed stream (101), although the channel for the feed stream (101) through the valve manifold has been switched to be a direct input from the feed stream (101) rather than from the first column (1). The outlet from the second column (2) is directed, through the valve manifold by appropriate actuation of valves (108), to the inlet of the next column (3) in the series. The continuous flowthrough from the outlets of the columns are diverted through the waste line (107), except where recoverable product is being eluted from a column, in which case the throughput of the column is directed, through the valve manifold, to a product recovery line (106). It will be appreciated that the "waste" line (107) may in practice be more than one line, giving the operator more control over the output of the columns and providing a means for recovery of more than just the eluted product. For example, such auxiliary lines may be used for solvent recovery or recovery of any flowthrough that might be reusable (or might contain a recoverable reusable component).

Preferably, the valve actuation and consequent channel switching within the valve manifold is coordinated along the whole series of columns. More preferably, the valve switching is controlled by a computer program, so that the switching occurs automatically, and the successive stages of capture chromatography are performed without interruption or system downtime. Such programmable switching and automated, coordinated switching is achieved in the aforementioned BioSMB™ purification system. Accordingly, the BioSMB™ system, or a coordinated system having its features, may be adapted to other unit operations in a biopharmaceutical purification process and thus provide equipment suitable for making all unit operations of a manufacturing process continuous processes.

Figure 10C:
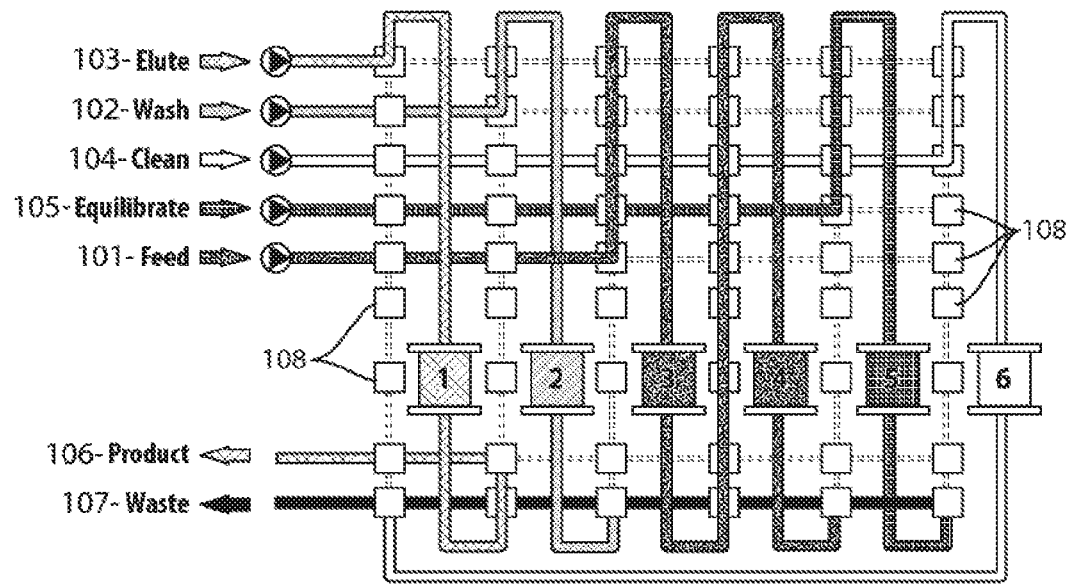

Referring to FIG. 10C, programmed switching of valves (108) in the valve manifold changes the input received by the first column (1) to the elution buffer stream (103). The captured biological product immobilized on the first column (1) begins to be eluted from the column, and appropriate switching of valves (108) downstream of the column (1) outlet directs the flowthrough (eluate) from the column (1) to the product recovery line (106). The solution directed along the product recovery line (106) is advantageously transferred to the succeeding unit operation (not shown). As an example, referring to the manufacturing process illustrated by FIG. 2A for an antibody product, the columns would be packed with chromatography media suitable for antibody capture, such as Protein A/sepharose, and the solution recovered from the recovery line (106) will contain the desired product (antibody) but may also be a low pH solution, e.g., if the elution buffer (103) is a low pH buffer (pH 3.0-pH 3.5), which is a typical means for eluting antibody from a Protein A affinity column. Thus, if the target product is received in a low pH solution, the succeeding unit operation may include a buffer exchange to readjust pH (since antibody will eventually denature at low pH), or prior to pH readjustment a low pH unit operation may be fed directly from the capture chromatography unit operation. As illustrated in FIG. 2A, an advantageous low pH unit operation for antibody biopharmaceutical processing is continuous low pH viral inactivation. Accordingly, an advantageous pair of successive unit operations in a protein biological product production process will comprise a capture chromatography unit operation followed by a low pH virus inactivation unit operation.

Referring again to FIG. 10C, at the same time the product is being eluted from the first column (1) after switching its input to the elution buffer (103), the input to the second column (2) in the series was switched to the wash buffer (102). The third column (3) continues to be loaded with the feed stream (101) and its flowthrough is directed to the inlet for the fourth column (4) of the series.

Figure 10D:
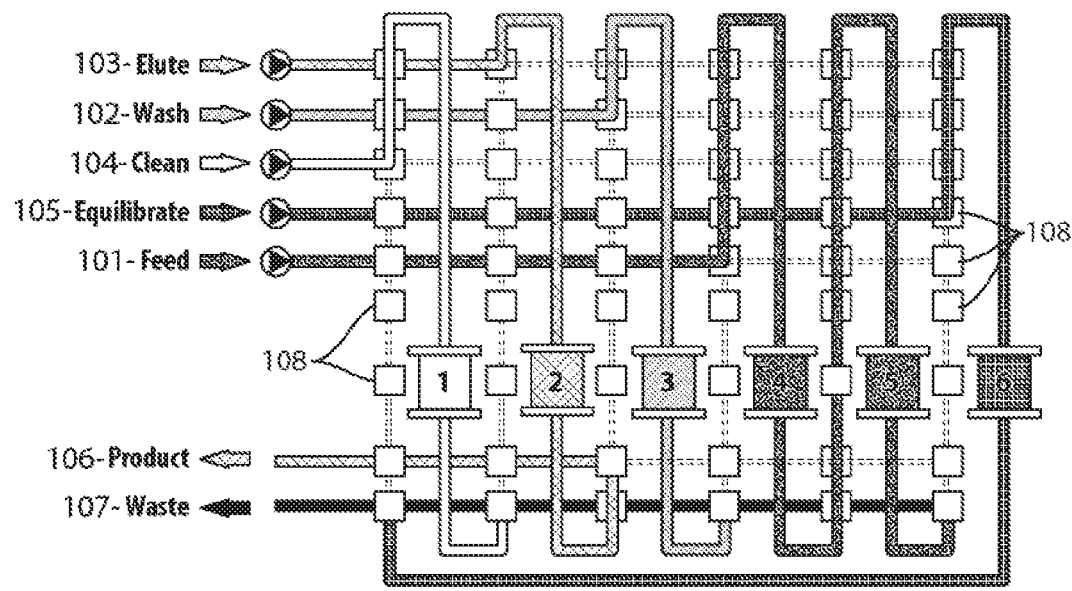

Referring to FIG. 10D, the next zone shift is illustrated, wherein the first column (1), now stripped of product, has its inlet switched, through the valve manifold, to receive a cleaning solution designed to regenerate the affinity media for another cycle of use; simultaneously, product-saturated column (2) after receiving wash buffer for one cycle (FIG. 10C), now receives the elution buffer (103), so that product is eluted from the column (2) and by appropriate actuation of valves (108) of the valve manifold is recovered through the product recovery line (106), and in a continuous processing system may be transferred directly to a downstream unit operation. The third column (3) in the series receives wash buffer (102) for the cycle illustrated here, and the fourth column (4) continues to be loaded with the teed stream (101) to achieve saturation of the column bed with product. Flowthrough from the fourth column (4) is connected through the valve manifold directly to the inlet for the fifth column (5) to begin loading of that column with product.

Figure 10E:
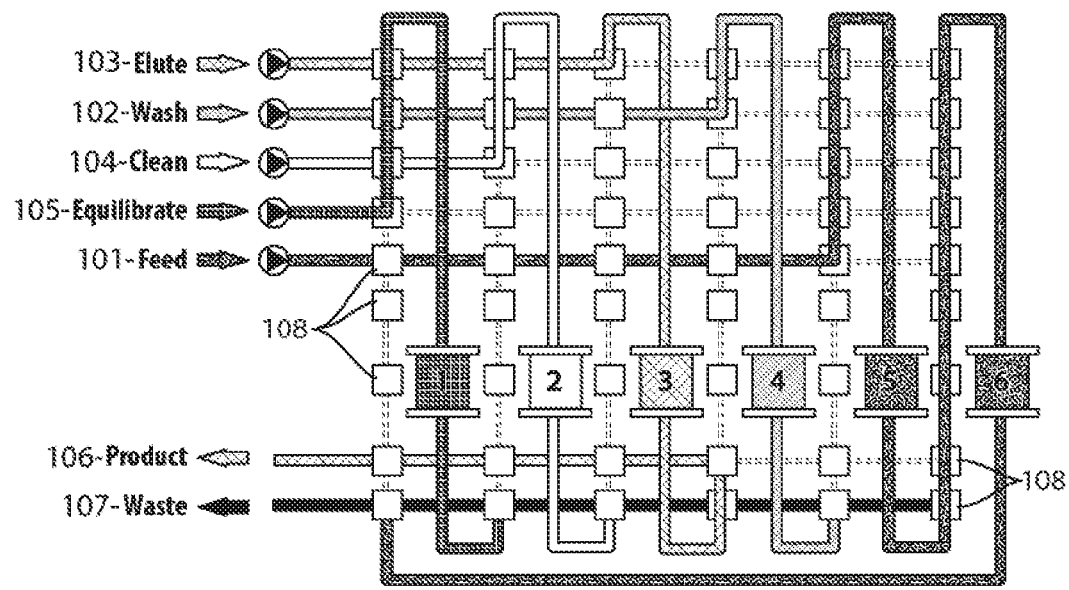

Referring to FIG. 10E, the next zone shift after the cycle shone in FIG. 10D is illustrated, wherein the first column (1), now stripped of product and cleaned to reactivate affinity ligand, has its inlet switched, through the valve manifold, to receive an equilibration buffer (106) designed to prepare the affinity media for another cycle of use, i.e., to receive the feed stream (101) in the next cycle; simultaneously, the input lines are switched through the valve manifold so that the fully eluted second column (2) now has its inlet connected to the cleaning solution (104). The product-saturated third column (3) after receiving wash buffer for one cycle (FIG. 10D), now receives the elution buffer (103), so that product is eluted from the column (3) and by appropriate actuation of valves (108) of the valve manifold is recovered through the product recovery line (106). In a continuous processing system, the product recovery line (106) may transfer the product solution directly to a downstream unit operation. The fourth column (4) in the series receives wash buffer (102) for the cycle illustrated here, and the fifth column (5) continues to be loaded with the feed stream (101) to achieve saturation of the column bed with product. Flowthrough from the fifth column (5) is connected through the valve manifold directly to the inlet for the sixth column (6) to begin loading of that column with product. After this cycle, a new cycle of purification, washing, elution, cleaning, and equilibration can begin, with valve switching of the feed stream to the inlet of the sixth column (6) and the outlet of the sixth column (6) being connected directly to the first column (1) in the series, so that product feed overflow from the preceding column (6) is captured on the regenerated, reequilibrated first column (1).

Continuous capture chromatography processes have been described above wherein the multicolumn operation of the chromatography process steps are regulated using an valve manifold "integrated circuit" of switchable channels, that is, an array of actuatable valves that can be programmed to create switching flowpaths for feeds to a series of columns in a multicolumn unit operation having several steps. For the purposes of illustration, such systems have been described in the context of a Protein A affinity chromatography separation of an antibody product from a feed stream, however it will be appreciated that such equipment as the illustrated valve array of FIGS. 10A-10E may be used in creating a multicolumn, continuous process for any type of chromatographic operation, including, size exclusion chromatography, ion exchange chromatography, affinity chromatography using another type of ligand than Protein A, metal ion chelation, hydrophobic interaction chromatography, and the like.

Continuous Low pH Virus Inactivation

As mentioned above, in designing a manufacturing process for a biopharmaceutical comprising a series of unit operations, an early step will commonly be a capture chromatography step. In the antibody production process illustrated in FIG. 2A a Protein A capture chromatography step proceeds directly after primary recovery of the antibody from the bioreactor. In many capture chromatography operations, in particular in Protein A affinity chromatography, elution from the affinity capture medium is accomplished by lowering the pH of the buffer flowing through the chromatography column. The Protein A/antibody complex dissociates at low pH, e.g., between about pH 3.0 and pH 3.5, Accordingly the eluate from a Protein A column is a low pH solution. An antibody product will suffer significant degradation if it resides at low pH for longer than 30 min. (±5 min.); on the other hand, low pH incubation is a very good method for inactivating viruses that may be present in the solution, Where an antibody product is intended for use as a pharmaceutical, viral inactivation is a mandatory step in the overall manufacturing process, and if the capture chromatography step results in a low pH eluate containing the antibody product, it will be advantageous in a continuous process to transfer the eluate directly to a unit operation designed for low pH virus inactivation.

Figure 11:
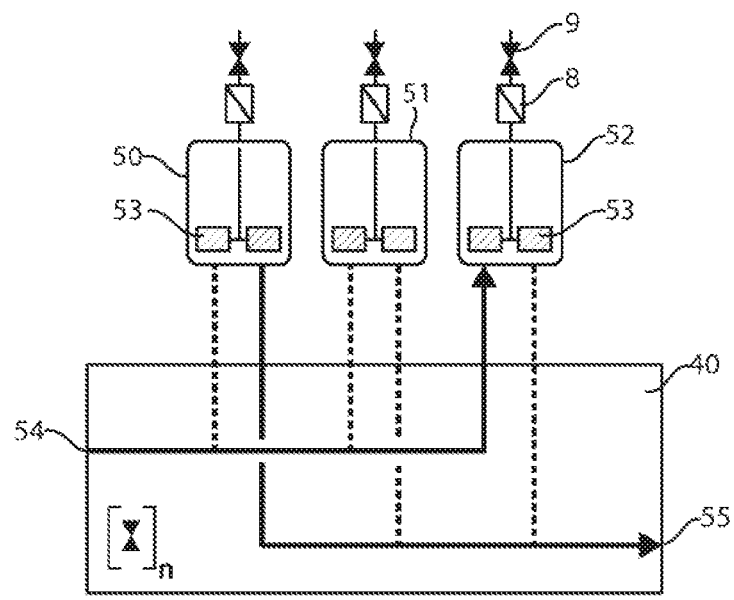
FIG. 11 is a schematic diagram of a unit operation requiring a product solution to be incubated for a time before being passed to a succeeding unit operation. An incubation unit operation may, for example, be used for protein refolding, for viral inactivation by incubation as lowered pH, or any other operation requiring the solution to be held at one stage for a predetermined incubation period before further processing. The unit operation illustrated in FIG. 11 utilizes a series of holding/incubation receptacles (50, 51, 52) with flow to each receptacle regulated through a common valve manifold (40). Where homogeneity of the mixture received in the holding/incubation receptacles (50, 51, 52) is desired, the receptacle may be equipped with means for keeping the contents thoroughly mixed, e.g., via mixing paddles (represented schematically by item 53), although any alternative mixing means (stirring bar, rocker table, shaker, etc.) may be used. The notation $[A]_n$ signifies that a sufficient array of valves, A, is present in the valve manifold (40) to direct the flow introduced via the inlet (54) independently to any of the holding/incubation receptacles and independently from any of the receptacles to an outlet (55) from the unit operation.

Referring to FIG. 11, a unit operation designed for continuous low pH virus inactivation is illustrated schematically. The unit operation is designed to receive a low pH feed (e.g., via inlet (54) into an integrated multi-valve valve block or manifold (40)) and transfer the feed to one of a series of holding/incubation receptacles (50, 51, 52). The valve manifold (4) is equipped with the channelling and valve array, represented by the figure $[A]_n$, appropriate for independent and alternative transfer to any of the holding/incubation receptacles (50, 51, 52) connected to the valve manifold (40). The object of the unit operation illustrated in FIG. 11 is to cause the product solution to be incubated at a pH suitable for inactivation of viruses that might be in the solution. For example, for an antibody product solution, incubation at a preselected, controlled pH (e.g., ±0.2 pH units) below pH 3.5 for 30 min. ±5 min., reduces the level of live viruses according to an accepted standard, and degradation or denaturation of the antibody product will be acceptable. Viral inactivation steps are typically designed to provide a log reduction value of 3 or higher, i.e., at least a 10,000-fold reduction in live viruses.

Referring again to FIG. 11, an aliquot of the product solution is transferred via the inlet (54) to an incubation receptacle (52), The receptacle may be sized to receive the transfer of all or any part of the throughput of the preceeding unit operation. In a continuous process utilizing disposable equipment, the receptacles (50, 51, 52) may advantageously be plastic bags, bottles, flasks, or the like. Likewise, the other components of the system, such as the tubing leads to the valve manifold (40) and parts of the manifold itself may be made of single-use materials. For example, the valve system may be formed by a replaceable sheet membrane covering an array of valve actuators and associated channels, where juxtaposition of the flexible membrane results in a close system of valve-controlled channels, the pattern of which is determined by different combinations of opened and closed valves in the array. (See, e.g., the valve cassette featured in the BioSMB™ purification system (Tarpon Biosystems, Inc., Worcester, MA (US)).

To monitor the pH of the solution closely, each receptacle will be equipped with a pH sensor (not shown), as well as inlet ports (not shown) for receiving acidic and/or basic solutions for adjusting the pH to within a desired range. It may be important that the antibody product solution introduced into the receptacles (50, 51, 52) remains well mixed, e.g., so that accurate pH readings may be made and any pH adjustment affects the entire aliquot collected in the receptacle. In such instances, the receptacles will be equipped with mixing means, which are represented in FIG. 11 schematically by propeller-type mixing paddles (53), but which may alternatively be any means suitable for effecting the desired level of homogenization of the product solution, Magnetic mixing bars, swirl flasks, rocking tables, and the like are all suitable and contemplated herein.

Figure 12:
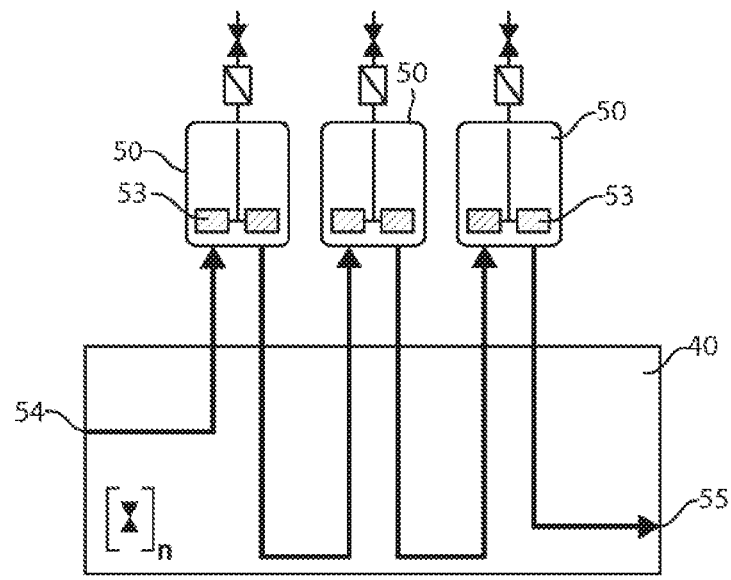
FIGS. 12 and 13 show alternative plans for series-connected holding/incubation receptacles (50), with flow regulated by the valve array, $[A]_n$ of a valve manifold (40). The embodiment of FIG. 12 illustrates that flow between series-connected receptacles (50) is regulated by the valve manifold (40). The embodiment of FIG. 13 illustrates a scheme wherein the flow through a series of three holding/incubation receptacles (50) occurs in succession, without the option for diverting flow to the outlet (55) before the throughput has passed through all three receptacles (50).
Figure 13:
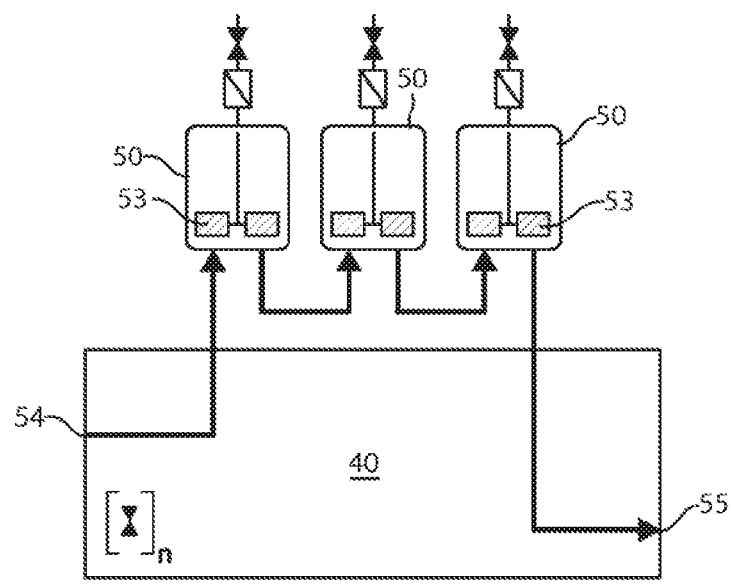

The variable intake channels through the valve module (40) can direct incoming flow to each of the holding/incubation receptacles (50, 51, 52). The contents of each of the incubation receptacles can be separately directed to the outlet (55) of this unit operation. In the diagram of FIG. 11, the solution entering the unit operation via inlet (54) is directed the third incubation receptacle (52), while the contents of the first incubation receptacle are being directed to the outlet (55), e.g., for transfer to the next unit operation. The dotted lines in FIG. 11 represent channels that are available but not in use, for directing solutions from the inlet (54) to the receptacles (50) and (51), and for directing the contents of receptacles (51) and (52) to the outlet (55), e.g., for transfer to the next unit operation. In addition to the lines illustrated, the valve module (40) may be provided with valving and pumps (not shown) for transferring solutions from one receptacle to another. This transfer through a series of receptacles might be implemented, for example, if a step-wise adjustment of pH or other solution condition is desired for this unit operation. In another embodiment, a first receptacle (52) can be used for incubation at a low pH, and then second and subsequent receptacles can be used for further processing, such as buffer exchange (e.g., to raise pH gradually), exposing the product to a chaotropic agent, or incubation to effect protein reassembly or refolding under solution conditions favorable for that. Referring to FIGS. 12 and 13, transfer of product solution through a series of three holding/incubation receptacles (50) in series is illustrated. In FIG. 12, the channels for transfer between holding/incubation receptacles (50) is depicted as flowing through the valve module (40), such that the serial transfer is controlled by manipulation of the integrated valve system. In FIG. 13, the serial transfer from one receptacle (50) to the next is not controlled using the valve module (40) but occurs by some other means, e.g., by overflow, manual transfer, or transfer triggered by a sensor in the source receptacle, e.g., a timer, a fill level sensor, or a pH sensor that signals a transfer operation when a particular pH is reached.

The acceptable time window for exposure of a proteinaceous product to low pH is typically narrow (e.g., 30±5 minutes). Exposure times that are too short do not provide sufficient viral inactivation, and exposure times that are too long lead to higher levels of degradation of the product. Continuous processing permits operating a low pH viral inactivation unit operation within tight time tolerances, A preferred methodology involves moving "packets" or aliquots of a product solution through the unit operation in a semi-continuous manner. Where the unit operation preceding the low pH viral inactivation step is a capture chromatography operation (e,g., Protein A affinity chromatography, for an antibody product), the product enters the low pH virus inactivation unit operation as a continuous series of eluate peaks. By pooling the number of eluate peaks for low pH processing that can be collected within the predetermined incubation period (e.g., 30 min. ±5 min. in the examples discussed above), the proper incubation time is imposed and a continuous transfer out to the next unit operation can be implemented.

By way of example, in a system for continuous viral inactivation where the product feed is a monoclonal antibody eluted from a Protein A chromatography column, the viral inactivation unit operation may be advantageously conducted as follows:

1. Eluate from Protein A will have a pH in the range of pH 3.5-pH 4.5. After collection of the pool to be processed (e.g., elution peaks from Protein A over a period equal to the low pH incubation period), the pH will be adjusted in the holding/incubation receptacle to the low pH viral inactivation conditions (e.g., pH 3.3) by titration with acid;
2. Acid titration will be accomplished by adding dilute acid (e.g., 1M HCl) until the pH setpoint for the low pH viral inactivation has been achieved with gentle mixing and continuous pH monitoring;
3. Once the appropriate pH has been reached, the product solution contents in the receptacle will be held for the required inactivation time (e.g., 30 min.);
4. After the required incubation time, another pH adjustment step will be used (preferably after transfer to another (downstream) holding receptacle) to bring the pH of the inactivated solution up to a pH (e.g., pH 5.0) suitable for transfer to a subsequent unit operation, such as loading onto a cation exchange chromatography column (see, e.g., FIG. 2A, item 13);
5. After the product solution has been transferred to the next unit operation, the holding receptacle(s) can be cleaned and rinsed for loading with another Protein A eluate pool, or the receptacle(s) can be discarded and fresh receptacles connected to the system to receive subsequent Protein A eluate pools and carry them through the low pH inactivation step.

To avoid physical transfer of the product solution from receptacle to receptacle, the "movement" of a receptacle containing the pooled Protein A eluate that is described in the sequence above can be achieved with a suitable controller and valve cassette. This is directly analogous to the simulated "movement" of chromatography columns achieved using the valve cassette in the system illustrated in FIG. 10A-FIG. 10E.

In an alternative embodiment, the Protein A eluate can be flowed through a cascading series of continuously mixed holding bags (receptacles), the first of which would accomplish the pH adjustment of the Protein A eluate, and the last of which would accomplish the pH readjustment of the inactivated solution prior to the next unit operation. The bags are sized to ensure that the appropriate residence time for low pH viral inactivation is achieved.

Continuous Processing Design

It may be appreciated that in order to effectively link unit operations of an overall manufacturing process so that they can be run in a continuous manner, quantitative analysis of the performance at each stage of the operation is necessary. Analytical methods for yield and purity of the product must be developed and implemented. Such methods may include an SDS-PAGE (reduced and non-reduced) method to assess product purity throughout the process, a host cell protein ELISA to assess clearance of host cell proteins by the purification process, and an HPLC or ultraviolet absorbance methods to determine product concentration and yields.

The design of a multicolumn counter-current continuous chromatography process, such as a SMB process, requires the same basic process information as for a batch process. This includes the product concentration in the feed solution (titer), the equilibrium binding capacity (static binding capacity) and the overall process sequence. Information about the mass transfer kinetics, which depend on the chromatography media, product and solution conditions, is also required for sizing the system. Generally, this can be obtained from breakthrough curve analysis. For this reason, a well-designed batch process is a very good starting point for the design of a continuous multicolumn or multistage purification process.

For a low pH inactivation step, analytical methods are needed for determination and confirmation of the acceptable time range for virus inactivation. For an ultrafiltration/diafiltration (UF/DF) step (see FIG. 2A, item 14), useful data can be obtained from a bench scale tangential flow filtration (TFF) system on flux as a function of transmembrane pressure at varying flow rates and product concentrations. For a nanofiltration and final 0.2 micron filtration steps (see FIG. 2A, items 16 and 17), useful data can be obtained on pressure drop as a function of flux and on loading capacity for each membrane device.

Using such batch process data obtained for each unit operation of the process, a continuous processing operation can be designed. The first design choice is the processing time. Contrary to a batch process, where the processing time is a result of the process design, a continuous process allows preselection of the processing time. The longer the processing time, the lower the flow rates through the unit operation series and the more compact the overall system can be (in terms of the scale of equipment utilized). On the other hand, processing times that are too long may result in product degradation at some stages that reach unacceptable levels. The feed flow rate is a result of the volume that needs to be processed and the processing time. The volume that needs to be processed is referred to as the "batch" or "lot size".

The minimum feed flow rate into the CPT process, $Q_m$, is calculated from the maximum processing time, t, using the following equation:

$$Q_m\left(\frac{mL}{min}\right) = \frac{A_p(g)}{C_p\left(\frac{g}{L}\right) * Y} * \frac{1}{60\left(\frac{min}{hr}\right) * t(hr)}$$

where $A_p$ is the amount of product required; $C_p$ is the product concentration in the feed; and Y is the overall process yield. Assuming the initial titer of an antibody product in cell culture supernatant is 1 g/L, and the overall process yield of the purification process is 60%, the minimum feed flow rate to achieve the 3 day, 100 g productivity objective is 39 mL/min. In order to ensure that the system can operate to comfortably achieve the productivity goal, the target CPT process feed flow rate will be set at a value at least 10% higher than the minimum flow rate, or about 45 mL/min.

Once the feed flow rate has been determined, the CPT process design can begin with the design of the first unit operation, for example a capture step such as a Protein A affinity chromatography step. For a continuous SMB chromatography step, the design algorithm starts with determining the minimum (simulated) transport rate of the chromatography media. This is the transport rate of the media that would allow binding all product in case there would be no mass transfer resistance, in case there would be ideal plug flow and in the absence of any other non-ideal parameters. In order to accommodate mass transfer resistance and deal with other non-ideal factors or limits, the actual simulated transport rate of chromatography media is chosen to be above the minimum transport rate. Typically, the practitioner selects safety margins in the range of 5-40%. The volume of chromatography media in the loading zone then depends on the flow rate going through the columns in the loading zone and the required residence time, which mainly depends on mass transfer phenomena such as diffusion. Knowing the required residence time and the feed flow rate, the required resin volume in the loading zone can be calculated.

Once the design for the first unit operation has been completed, the outlet product flow rate from this step can be set to equal the inlet flow rate for the second unit operation in the process, so that the hydraulic capacities of each connecting step are matched. Similar design algorithms as for the first unit operation can be applied to each unit operation in the process. Batch data for each unit operation can be used to develop a continuous operation design for that unit operation, which allows it to be linked to the previous and subsequent unit operations. When this process is completed for all unit operations in the overall purification process, the initial CPT process design is complete. From this initial design, suitable equipment and disposables for all steps of the manufacturing process can be sized, specified, and ordered to fit the parameters and demands of the initial CPT design.

Once the initial design has been established, each process step can then be optimized through iterative experimentation to maximize any desired attribute, such as volumetric productivity or buffer utilization.

In order to establish a seamless streamlined continuous process, the size and throughput of each unit operation will be governed by the flow rate (hydraulic capacity) instead of by total volume or mass to be processed. For each step, optimization will involve a study of the principles and phenomena that govern size and hydraulic capacity of the unit operation. For instance, the optimization of the chromatography steps using continuous multicolumn SMB will involve a study of the impact of the separation factor, S, and number of transport units, NTU, on performance of the process step.

The separation factor, S, is a measure of transport capacity caused by the bed transport rate in relation to the product feed rate and is defined as:

$$S = \frac{(\phi_{bsd} * Q_{static})}{[(\phi)]_{feed} * C_{feed})}$$

where $\emptyset_{feed}$ and $\emptyset_{bed}$ are the flow rates of the liquid and stationary phases respectively (in the case of the bed, $\emptyset_{bed}$ is the simulated transport rate), $Q_{static}$ is the binding capacity of the media, and $C_{feed}$ is the concentration in the feed.

The number of transfer units, NTU, is used as a measure of he mass transfer kinetics for countercurrent chromatography systems and is defined as:

$$NTU = k_{oL} \times a \times V/\Phi_{feed}$$

where $k_{oL}$ is the overall mass transfer coefficient of the system, V is the column volume, and a is the specific surface area, which equals the surface area of the particles divided by column volume. The NTU is the ratio of the residence time in the system and the characteristic mass transfer time, Through experimental studies evaluating performance at different values of NTU and S, the optimal processing conditions can be identified for each step, in order to achieve the desired productivity while meeting the separation or performance objectives (e.g., host cell protein removal for a Protein A chromatography step). In addition to this optimization, it will be advantageous to investigate the stability of the unit operation and the sensitivity to disturbances, in order to establish some preliminary parameters for robustness of the integrated process. For example, the optimal processing conditions may be too close to conditions that would result in unacceptable performance, in which case the conditions are adjusted to provide optimal and acceptably robust performance.

Finally, during this stage, particular attention should be paid to the pressure drop of each individual unit operation. As this may become a limiting factor in the cascade of unit operations, the installation of surge receptacles will be an important device for equalization of system pressure at critical points in the cascade and thereby adjusting the pressure drop required to maintain a desired downstream flow rate.

The robustness of each step to inlet feed rates will be important to ensure the ability to adapt to the range of operating conditions that will be experienced during actual operation. Included in this objective is the development of shut-down and start-up procedures for an entire continuous line, including procedures for use of emergency collection receptacles described herein.

During continuous operation of the manufacturing process, samples may be taken at each point in the process to verify that the anticipated product and process attributes (i.e., purity, yield) are being achieved by the CPT process. Final purified bulk product may be analyzed to determine product purity by SDS-PAGE and HPLC, clearance of specific impurities (e.g., host cell proteins) by ELISA, and product concentration to enable overall yield determination.

REFERENCES

Rosset A J, Neuzil R W and Broughton D B. Industrial application of preparative chromatography, in: Rodrigues A E, Tondeur D (eds.), Percolation Processes: Theory and Application, Rockville, MD, Sijthoff & Noordhoff Press; 1981.

Van Walsem H J and Thompson M C, Simulated moving bed in the production of lysine, J. Biotech, 1997; 59:127-132.

Trout B and Bisson W, Continuous manufacturing of small molecule pharmaceuticals: the ultra lean way of manufacturing, presented at MIT Leaders for Global Operations Conference; Cambridge, MA; Dec. 3-4, 2009.

Bisschops M et al, Single-use continuous, counter-current, multicolumn chromatography. BioProcess International, June 2009; 7(Supp 5):18-23.

Coffman J. Development of a Protein A SMB step for a Mab with up to 10 titers, presented at BioManufacturing and Development conference; Boston, MA; Nov. 1-3, 2010.

From the foregoing description it is evident that flexible and serviceable continuous processing methods can be implemented to make virtually any biopharmaceutical manufacturing process more efficient and less costly to run. The continuous processing features described herein also allow the run time of manufacturing processes to be significantly compressed.

Although a number of embodiments have been described above, it will be understood by those skilled in the art that modifications and variations of the described processes and apparatuses may be made without departing from the disclosure of the invention or the scope of the appended claims. The articles and publications cited above are hereby incorporated by reference.

What is claimed is:

1. A continuous processing system comprising:
(a) a first apparatus for carrying out a first unit operation comprising:
(1) a plurality of valve modules, each module having a central channel traversing the module and a plurality of branch channels connecting the central channel with an outside of the valve module, wherein each of the channels has at least one independently actuatable valve for independently opening or closing the channel, wherein the valve of the central channel separates an inlet end of the central channel from an outlet end of the central channel, wherein at least two branch channels connect separate inlets to the valve module with the central channel on an inlet side of the central channel valve and at least two branch channels lead from the central channel on an outlet side of the central channel valve to separate outlets from the valve module;
(2) a plurality of solution conduits, each conduit connecting to a separate branch channel of each valve module, and
(3) a plurality of chromatography columns, each column having an inlet and an outlet, wherein the column inlet is connected to the inlet end of a valve module central channel and the column outlet is connected to the outlet end of the central channel of a different valve module, such that the plurality of columns is connected in series through intervening valve modules and wherein the outlet of the last column in the series is connected, via an intervening valve module, to the inlet of a first column in the series;
(b) a second apparatus for carrying out a second unit operation comprising:
(1) one or more incubation receptacles each having at least one inlet and at least one outlet, wherein collectively the one or more incubation receptacles has at least the capacity to hold an output of the first unit operation;
(2) a valve module comprising an inlet and an outlet, an inlet channel connected to the valve module inlet, and one or more inlet branch channels connecting with the inlet channel, wherein each inlet branch channel leads from the inlet channel and connects to an inlet of one of the one or more incubation receptacles, wherein each of the inlet branch channels has at least one independently actuatable valve for independently opening or closing the channel, the valve module further comprising an outlet channel leading to the valve module outlet, and one or more outlet branch channels connecting with the outlet channel, wherein each outlet branch channel leads from the outlet channel and connects to an outlet of one of the one or more incubation receptacles, wherein each of the outlet branch channels has at least one independently actuatable valve for independently opening or closing the channel; and
(c) a third apparatus, for connecting the output of the first apparatus to the inlet of the second apparatus, the third apparatus comprising:

(1) a valve module providing at least five fluid transmission channels comprising a central channel traversing the valve module and having an inlet end and an outlet end, a priming channel connecting a separate inlet with the central channel, a surge receptacle inlet channel connecting a separate inlet with the central channel, a surge receptacle outlet channel connecting a separate outlet with the central channel, and a bypass channel connecting a separate outlet with the central channel, each of the five channels having at least one independently actuatable valve for independently opening or closing the channel, wherein the central channel inlet is connected to an outlet branch channel of each of the plurality of valve modules of the apparatus of the first unit operation, the priming channel inlet being suitable for receiving fluid for filling the priming channel and the central channel, (2) at least one surge receptacle for regulating flow between unit operations and relieving back pressure, the surge receptacle having at least one inlet and at least one outlet, wherein the at least one inlet of the surge receptacle is connected to the surge receptacle outlet channel of the valve module, and the at least one outlet of the surge receptacle is connected to the surge receptacle inlet channel of the valve module, and wherein the at least one surge receptacle has the capacity to hold the output of the apparatus of the first unit operation, and wherein the central channel outlet of the valve module is connected to the inlet of the valve module of the apparatus for carrying out the second unit operation;

wherein the at least one surge receptacle further comprises a vent outlet, the vent outlet communicating an inside of the receptacle with the ambient environment.

2. The apparatus of claim 1, wherein a filter is interposed between the vent outlet and the ambient environment, and the vent outlet further comprises a valve for opening and closing the outlet.

3. The apparatus of claim 1, wherein the connection between the at least one outlet of the surge receptacle and the surge receptacle inlet channel of the valve module is equipped with a pump for regulating fluid flow along the connection.

4. The apparatus of claim 1, wherein the bypass channel outlet is connected to a bypass collection receptacle having the capacity to hold the throughput of a unit operation connected to the valve manifold central channel inlet.

5. The apparatus of claim 4, wherein the surge receptacle outlet is connected to a pump.

6. The apparatus of claim 4, wherein the bypass channel outlet is connected to a bypass collection receptacle having the capacity to hold the throughput of a unit operation connected to the valve manifold central channel inlet.

7. The apparatus of claim 4, wherein a filter is interposed between the vent outlet and the ambient environment, and the vent outlet further comprises a valve for opening and closing the outlet.

8. A continuous processing system comprising:
(a) a first apparatus for carrying out a first unit operation comprising:
(1) a plurality of valve modules, each module having a central channel traversing the module and a plurality of branch channels connecting the central channel with an outside of the valve module, wherein each of the channels has at least one independently actuatable valve for independently opening or closing the channel, wherein the valve of the central channel separates an inlet end of the central channel from an outlet end of the central channel, wherein at least two branch channels connect separate inlets to the valve module with the central channel on an inlet side of the central channel valve and at least two branch channels lead from the central channel on an outlet side of the central channel valve to separate outlets from the valve module;

(2) a plurality of solution conduits, each conduit connecting to a separate branch channel of each valve module, and (3) a plurality of chromatography columns, each column having an inlet and an outlet, wherein the column inlet is connected to the inlet end of a valve module central channel and the column outlet is connected to the outlet end of the central channel of a different valve module, such that the plurality of columns is connected in series through intervening valve modules and wherein the outlet of the last column in the series is connected, via an intervening valve module, to the inlet of a first column in the series;

(b) a second apparatus for carrying out a second unit operation comprising:
(1) one or more incubation receptacles each having at least one inlet and at least one outlet, wherein collectively the one or more incubation receptacles has at least the capacity to hold an output of the first unit operation;

(2) a valve module comprising an inlet and an outlet, an inlet channel connected to the valve module inlet, and one or more inlet branch channels connecting with the inlet channel, wherein each inlet branch channel leads from the inlet channel and connects to an inlet of one of the one or more incubation receptacles, wherein each of the inlet branch channels has at least one independently actuatable valve for independently opening or closing the channel, the valve module further comprising an outlet channel leading to the valve module outlet, and one or more outlet branch channels connecting with the outlet channel, wherein each outlet branch channel leads from the outlet channel and connects to an outlet of one of the one or more incubation receptacles, wherein each of the outlet branch channels has at least one independently actuatable valve for independently opening or closing the channel; and (c) a third apparatus, for connecting the output of the first apparatus to the inlet of the second apparatus, the third apparatus comprising:
(1) a valve manifold providing at least three fluid transmission channels comprising a central channel traversing the valve manifold and having an inlet end and an outlet end, a priming channel connecting a separate inlet with the central channel, and a bypass channel connecting a separate outlet with the central channel, each of the channels having at least one independently actuatable valve for independently opening or closing the channel, the central channel inlet being suitable for receiving throughput from an upstream unit operation, and the priming channel inlet being suitable for receiving fluid for filling the priming channel and the central channel, (2) at least one surge receptacle for regulating flow between unit operations and relieving back pressure, the surge receptacle having at least one inlet and at least one outlet, the at least one inlet of the surge receptacle being connected to the central channel outlet of the valve manifold, and the at least one surge receptacle having the capacity to hold the throughput of a unit operation connected to the valve manifold central channel inlet;

wherein the surge receptacle further comprises a vent outlet, the vent outlet communicating an inside of the receptacle with the ambient environment.

\* \* \* \* \*